(12) United States Patent
Hancock et al.

(10) Patent No.: US 11,151,505 B1
(45) Date of Patent: Oct. 19, 2021

(54) AUTOMATIC ANALYSIS OF ORGANIZATION PROCESS/OPERATIONS DATA

(71) Applicant: Accenture Global Solutions Limited, Dublin (IE)

(72) Inventors: RaeAnn J. Hancock, Virginia Beach, VA (US); Scott Alister, Naperville, IL (US); Marjorie P. Bogaert, Clayton, CA (US); Denise M. Brock, New Kensington, PA (US); Amber Brockington, Philadelphia, PA (US); Doreen Colburn, Millbrook, AL (US); Aakash R. Desai, Oak Park, IL (US); John M. Froehlich, Benicia, CA (US); Betty J. Gillespie, Grand Island, NY (US); Ninad Gokhale, Pune (IN); Amit Jindal, Palo Alto, CA (US); Daniel Huedig, Schweich (DE); Brian P. Kalis, Savage, MN (US); Franklin C. Lee, San Francisco, CA (US); Thomas N. Mangan, Johns Creek, GA (US); Gerald J. Meklaus, West Chester, PA (US); Aaron Morrow, Lee's Summit, MO (US); Jennifer Nichol, Lakeland, FL (US); Milind Pawar, Saratoga, CA (US); Douglas Pedersen, Boulder, CO (US); Frank Pino, Cream Ridge, NJ (US); Ann Turner, Hollis, NH (US); Cristi Velastegui, San Anselmo, CA (US); Joseph Wee, Daly City, CA (US)

(73) Assignee: Accenture Global Solutions Limited, Dublin (IE)

( * ) Notice: Subject to any disclaimer, the term of this patent is extended or adjusted under 35 U.S.C. 154(b) by 534 days.

(21) Appl. No.: 15/789,722

(22) Filed: Oct. 20, 2017

Related U.S. Application Data

(60) Provisional application No. 62/517,622, filed on Jun. 9, 2017.

(51) Int. Cl.
   *G06Q 10/06* (2012.01)

(52) U.S. Cl.
   CPC ....... *G06Q 10/067* (2013.01); *G06Q 10/0637* (2013.01)

(58) Field of Classification Search
   CPC .......................... G06Q 10/067; G06Q 10/0637
   (Continued)

(56) References Cited

U.S. PATENT DOCUMENTS

| 2012/0116800 | A1* | 5/2012 | McCallie | G06F 19/325 |
| --- | --- | --- | --- | --- |
| | | | | 705/2 |
| 2015/0066538 | A1* | 3/2015 | Dantsker | G16H 10/60 |
| | | | | 705/3 |

(Continued)

OTHER PUBLICATIONS

Violino, IT Gets Some Smarts: Intelligence Techniques Uncover the Business Value of Information Systems, 23 Manufacturing Business Technology 6 (2005) (Year: 2005).*

*Primary Examiner* — Charles Guiliano
(74) *Attorney, Agent, or Firm* — Harrity & Harrity, LLP

(57) ABSTRACT

A device may receive data associated with one or more healthcare organizations. The data may relate to a performance of one or more processes or operations of the one or more healthcare organizations. The device may process the data using one or more techniques to permit mapping of the data to a healthcare operating model. The device may map the data to the healthcare operating model. The healthcare operating model may be used to perform one or more analyses of the one or more processes or operations of the one or more healthcare organizations. The device may perform one or more analyses of the data to identify one or (Continued)

more deficiencies related to the one or more processes or operations. The device may perform one or more actions to positively impact the performance of the one or more processes or operations of the one or more healthcare organizations.

20 Claims, 23 Drawing Sheets

(58) Field of Classification Search
USPC .......................................................... 705/7.36
See application file for complete search history.

(56) References Cited

U.S. PATENT DOCUMENTS

| 2015/0120621 A1* | 4/2015 | Alkov | ................ | G06F 16/3329 |
| | | | | 706/12 |
| 2016/0078382 A1* | 3/2016 | Watkins | ................ | H04L 43/065 |
| | | | | 705/7.25 |

* cited by examiner

AUTOMATIC ANALYSIS OF ORGANIZATION PROCESS/OPERATIONS DATA

RELATED APPLICATION(S)

This application claims priority under 35 U.S.C. § 119 to U.S. Provisional Patent Application No. 62/517,622, filed on Jun. 9, 2017, the content of which is incorporated by reference herein in its entirety.

BACKGROUND

A process may include a set of interrelated activities that interact to achieve a result. For example, a healthcare organization may implement a process related to operations of the healthcare organization, patients associated with the healthcare organization, and/or the like. A result of the process may be affected by a structure and/or organization of the process and/or the healthcare organization.

SUMMARY

According to some possible implementations, a device may include one or more processors to receive data associated with an organization. The data may relate to a performance of a process or operations of the organization. The data may relate to hardware resources of the organization used to implement the process or operations. The one or more processors may process the data using a technique comprising natural language processing. The technique may permit mapping of the data to an operating model. The one or more processors may map the data to the operating model after processing the data. The operating model may be used to perform an analysis of the process or operations of the organization. The one or more processors may perform the analysis of the data based on mapping the data to the operating model. The one or more processors may identify, based on performing the analysis, one or more of a deficiency related to the performance, or a manner in which to improve the performance. The one or more processors may perform an action to positively impact the performance of the process or operations of the organization based on identifying the deficiency or the manner in which to improve the performance.

According to some possible implementations, a method may include receiving, by a device, data associated with a healthcare organization. The data may relate to a performance of a plurality of processes or operations of the healthcare organization. The data may relate to a plurality of processing resources or computing resources of the healthcare organization used to implement the plurality of processes or operations. The method may include processing, by the device, the data using a plurality of techniques to permit mapping of the data to a healthcare operating model. The plurality of techniques may include natural language processing. The healthcare operating model may identify a plurality of functional areas or sub-areas of a particular healthcare organization. The method may include mapping, by the device, the data to the healthcare operating model after processing the data. The healthcare operating model may be used to perform a plurality of analyses of the plurality of processes or operations of the healthcare organization. The method may include performing, by the device, the plurality of analyses of the data based on mapping the data to the healthcare operating model. The method may include identifying, by the device, a plurality of deficiencies related to the performance based on performing the plurality of analyses. The method may include storing, by the device, the data, or information associated with the plurality of analyses, in a knowledge base based on identifying the plurality of deficiencies. The method may include performing, by the device, a plurality of actions to positively impact the performance of the plurality of processes or operations of the healthcare organization after storing the data or the information.

According to some possible implementations, a non-transitory computer-readable medium may store one or more instructions that, when executed by one or more processors, cause the one or more processors to receive data associated with one or more healthcare organizations. The data may relate to a performance of one or more processes or operations of the one or more healthcare organizations. The data may relate to one or more systems of the one or more healthcare organizations used to implement the one or more processes or operations. The one or more instructions, when executed by the one or more processors, may cause the one or more processors to process the data using one or more techniques to permit mapping of the data to a healthcare operating model. The one or more techniques may include natural language processing. The one or more instructions, when executed by the one or more processors, may cause the one or more processors to map the data to the healthcare operating model using one or more identifiers associated with the data after processing the data. The healthcare operating model may be used to perform one or more analyses of the one or more processes or operations of the one or more healthcare organizations. The one or more identifiers may identify one or more functional areas, or one or more sub-areas, of the one or more healthcare organizations with which the data is associated. The one or more instructions, when executed by the one or more processors, may cause the one or more processors to perform one or more analyses of the data to identify one or more deficiencies related to the one or more processes or operations based on mapping the data to the healthcare operating model. The one or more instructions, when executed by the one or more processors, may cause the one or more processors to perform one or more actions to positively impact the performance of the one or more processes or operations of the one or more healthcare organizations based on performing the one or more analyses.

DETAILED DESCRIPTION

The following detailed description of example implementations refers to the accompanying drawings. The same reference numbers in different drawings may identify the same or similar elements.

A healthcare organization, such as an accountable care organization and/or a provider and/or integrated delivery organization, may implement a process to perform a function of the healthcare organization. For example, the healthcare organization may implement a process to perform a reporting and/or assurance function, to perform a value analysis of the healthcare organization, to provide support services to a patient, and/or the like. The healthcare organization may lack a technique for efficiently and accurately performing a computer-based analysis of a performance of the process and/or the healthcare organization. In addition, the healthcare organization may lack a technique for comparing the performance of the process and/or operations of the healthcare organization to a threshold (e.g., a benchmark, an industry standard, an organization identified as a high-performing healthcare organization relative to other healthcare organizations), such as to identify a deficiency related to the performance.

Implementations described herein enable a recommendation platform to receive data associated with a performance of a process of a healthcare organization and/or operations of the healthcare organization, to analyze the data to identify a deficiency related to the performance of the process and/or operations and/or a manner in which to improve the performance, and/or to perform an action to positively impact the deficiency and/or to improve the performance.

In this way, the recommendation platform increases an efficiency of analyzing a process of a healthcare organization and/or operations of the healthcare organization. In addition, the recommendation platform improves an accuracy of a result and/or output of a process, thereby conserving processing resources that would otherwise be consumed due to inaccurate results and/or outputs. Further, the recommendation platform improves performance of a process and/or operations of a healthcare organization, thereby conserving processing resources and/or computing resources of devices used to implement the process and/or the operations.

FIGS. 1A-1D are diagrams of an overview of an example implementation 100 described herein. As shown in FIGS. 1A-1D, example implementation 100 includes one or more external information sources, a recommendation platform, and one or more client devices.

Figure 1A:
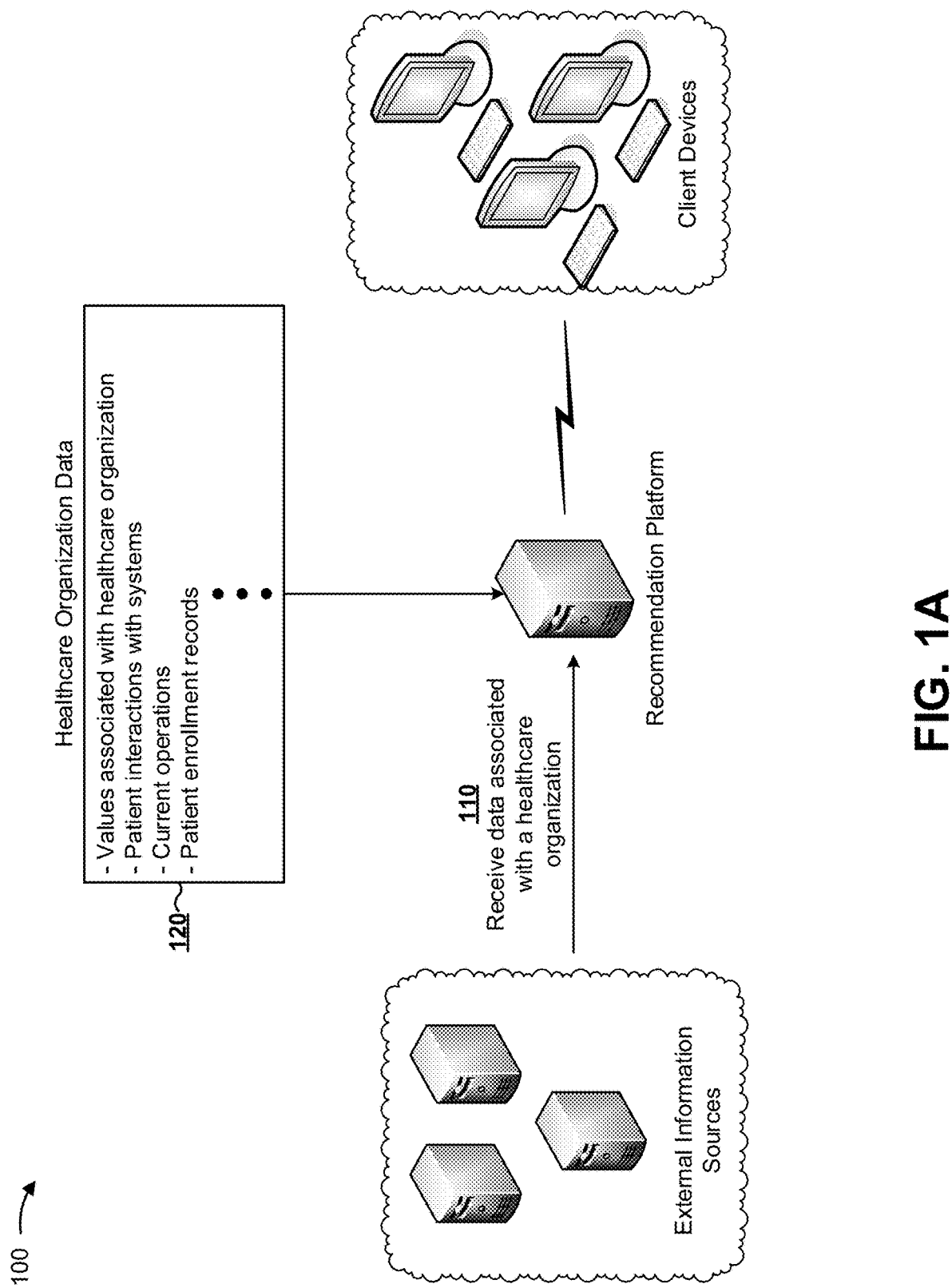
FIGS. 1A-1D are diagrams of an overview of an example implementation described herein.

As shown in FIG. 1A, and by reference number 110, the recommendation platform may receive, from the external information sources, data associated with a healthcare organization (e.g., healthcare organization data). For example, the data received may relate to performance of a process, may relate to operations of the healthcare organization, and/or the like. In some implementations, the recommendation platform may receive millions, billions, trillions, etc., of data elements when receiving the data.

As shown by reference number 120, the healthcare organization data may include values associated with the healthcare organization, data elements related to patient interactions with systems that the healthcare organization uses, data elements related to current operations of the healthcare organization, data related to patient enrollment records, and/or the like. In some implementations, the healthcare organization data may include patient population data, which may include aggregated and/or anonymized data that may be encrypted according to an encryption technique.

Figure 1B:
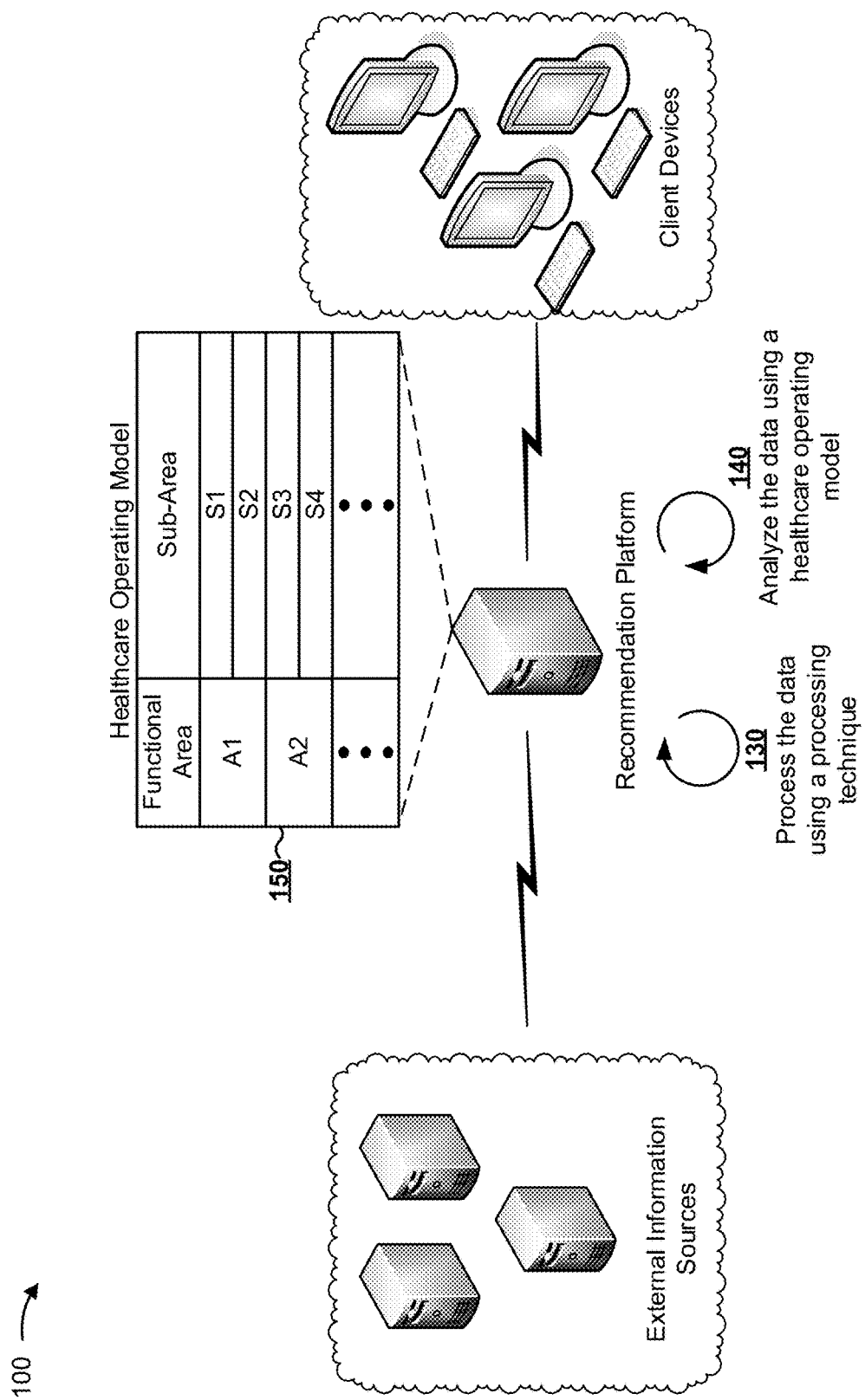

As shown in FIG. 1B, and by reference number 130, the recommendation platform may process the data using a processing technique. For example, the recommendation platform may process the data using natural language processing, artificial intelligence, machine learning, and/or the like. Continuing with the previous example, the recommendation platform may process millions, billions, trillions, etc. of data elements when processing the data received from the external information sources. In some cases, processing the data may include use of a big data analysis tool and/or technique.

As shown by reference number 140, the recommendation platform may analyze the data using a healthcare operating model. For example, the recommendation platform may map data to portions of the healthcare operating model to identify a manner in which the organization implements a process and/or operates. Additionally, or alternatively, and as another example, the recommendation platform may use the healthcare operating model to perform a comparison of the data and a threshold, such as to identify a deficiency of the healthcare organization relative to a benchmark or industry standard. In some implementations, the recommendation platform may analyze the data to identify a deficiency related to the performance of the process and/or operations of the healthcare organization.

An example of a healthcare operating model is shown by reference number 150. The healthcare operating model may represent a structure or organization of another healthcare organization (e.g., identified as a high-performing healthcare organization), a benchmark healthcare organization, a threshold, an industry standard, and/or the like. In some implementations, the healthcare operating model may identify functional areas of the healthcare organization (e.g., shown as A1, A2, etc.). For example, a functional area may relate to managing market and service lines of the healthcare organization, directing/planning/guiding the healthcare organization, channels and tools that the healthcare organization uses to implement a process and/or provide a service, processes of the healthcare organization, and/or the like.

In some implementations, the operating model may identify sub-areas corresponding to a functional area (e.g., shown as S1 and S2 as sub-areas of functional area A1, and S3 and S4 as sub-areas of functional area A2). For example, sub-areas corresponding to service lines of the healthcare organization may include clinical policy, consumer experience, and/or the like.

Figure 1C:
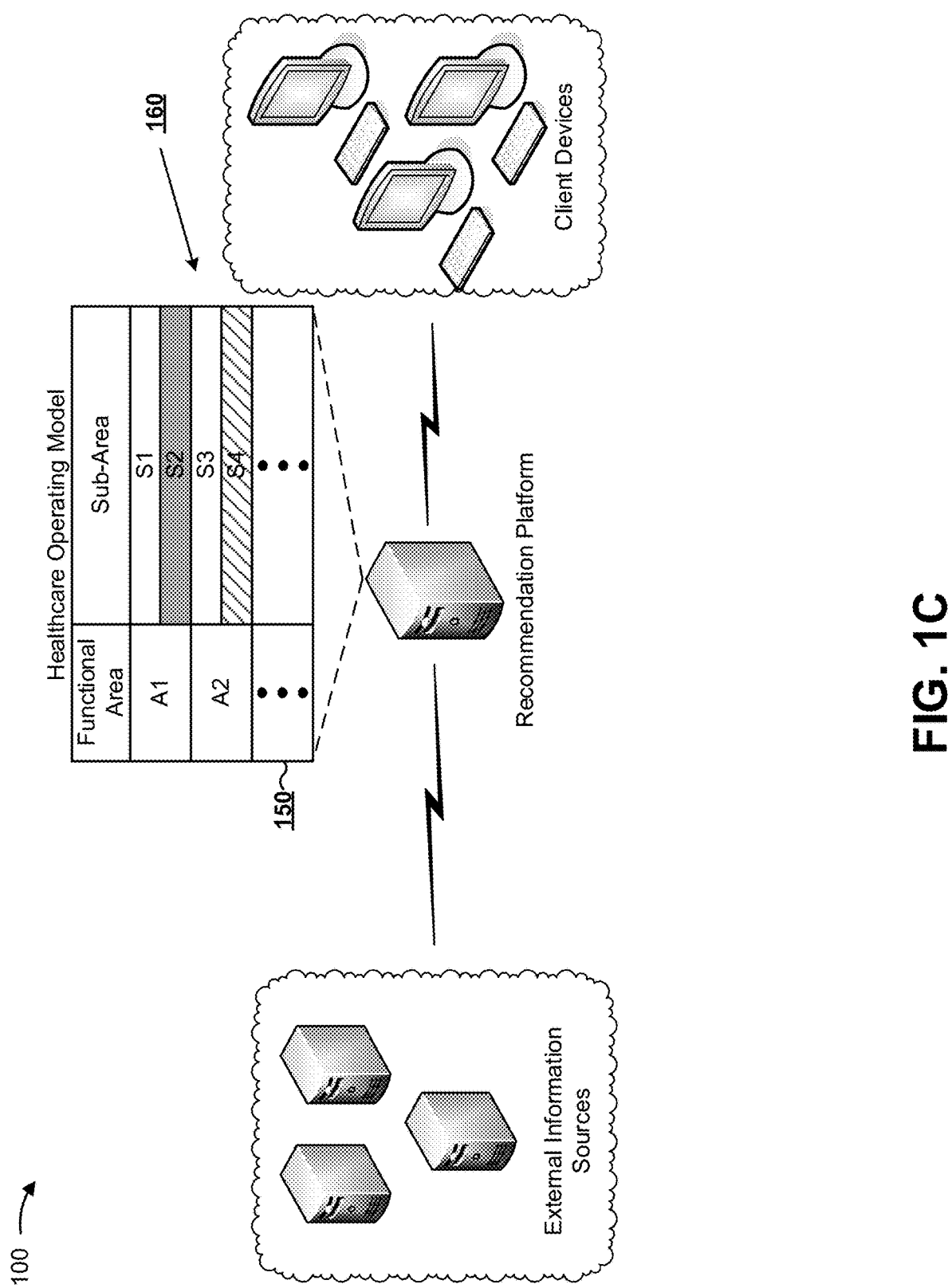

As shown in FIG. 1C, and by reference number 160, the recommendation platform may identify a deficiency related to performance of a process and/or operations of the healthcare organization and/or may identify a manner in which the healthcare organization can be improved. In some implementations, the recommendation platform may identify sub-areas without a deficiency (e.g., that satisfy a threshold or that do not satisfy a threshold that indicates a deficiency), as shown as white boxes (e.g., S1 and S3). In some implementations, the recommendation platform may identify sub-areas that have a deficiency (e.g., that satisfy a first threshold indicating a deficiency but not a second threshold indicating a more or less severe deficiency), as shown as a striped box (e.g., S4).

In some implementations, the recommendation platform may identify sub-areas that have a different deficiency (e.g., that satisfy a first threshold and a second threshold indicating a deficiency), as shown as a dark shaded box (e.g., S2). The recommendation platform may identify the deficiency using thresholds, information identifying an industry standard, and/or the like. In this way, the recommendation platform may identify a deficiency related to performance of a process and/or operations of a healthcare organization and/or identify a manner in which to improve the performance of the process and/or operations.

Figure 1D:
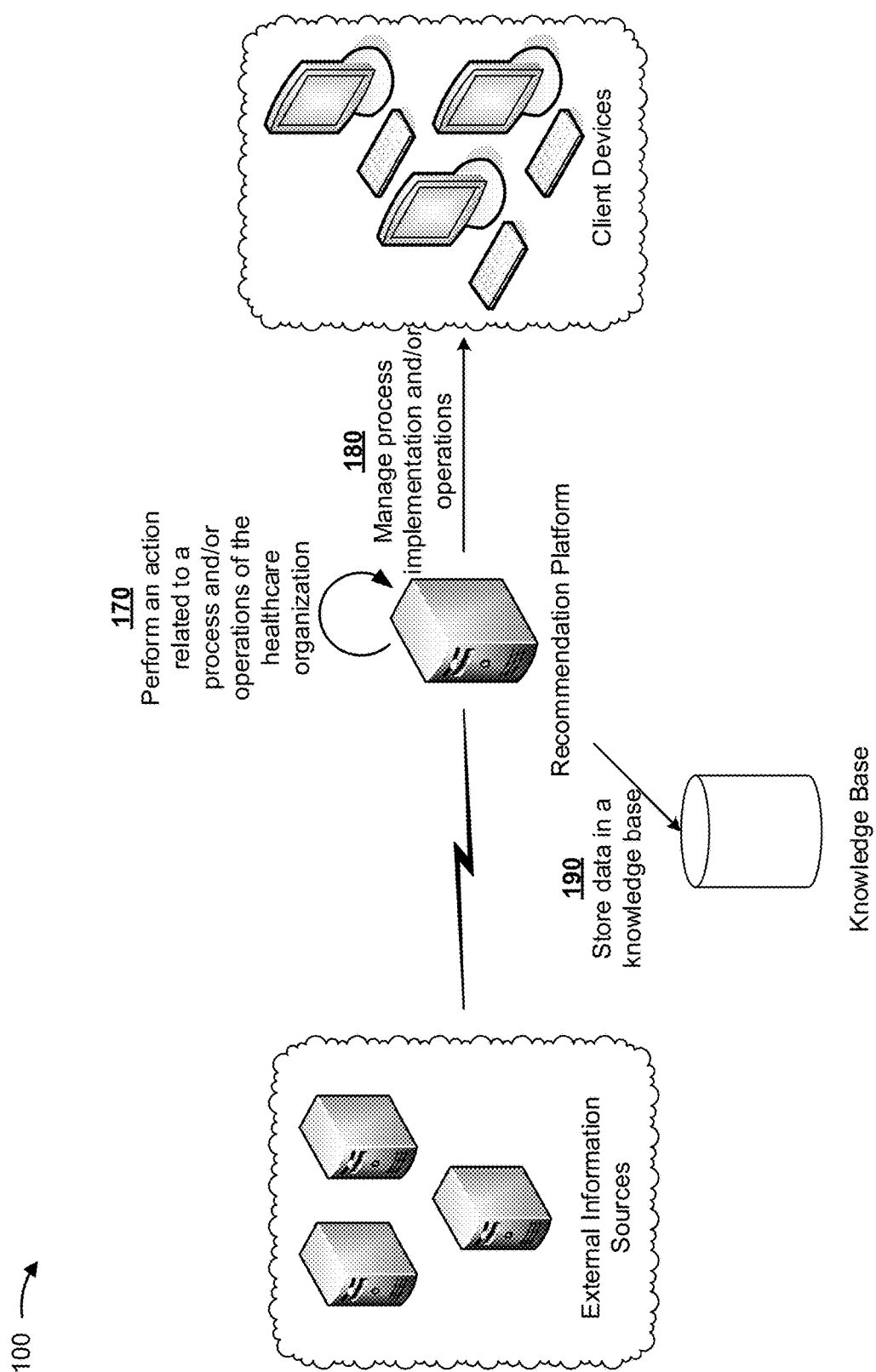

As shown in FIG. 1D, and by reference number 170, the recommendation platform may perform an action related to a process and/or operations of the healthcare organization. For example, the recommendation platform may perform an action to positively impact a deficiency related to a performance of the process and/or operations of the healthcare organization. For example, the recommendation platform may perform an action to reduce or eliminate a deficiency, to increase an efficiency of a process and/or operations of the healthcare organization (e.g., thereby conserving processing resources of devices that the healthcare organization uses to implement the process and/or operations), and/or the like.

As shown by reference number 180, the recommendation platform may manage implementation of a process and/or operations of the healthcare organization. For example, the recommendation platform may provide a set of instructions to one or more client devices to perform a process in a particular manner. Additionally, or alternatively, and as another example, the recommendation platform may gather data, relating to metrics, from the client devices and may adjust performance of the process and/or operations of the organization based on the metrics. Continuing with the previous example, the recommendation platform may dynamically adjust the performance of the process and/or operations (e.g., in real-time or near real-time as the recommendation platform receives data).

As shown by reference number 190, the recommendation platform may store the data associated with the analysis in a knowledge base (e.g., a knowledge graph). Additionally, or alternatively, the recommendation platform may store data gathered during management of the process and/or operations of the healthcare organization. In some implementations, the knowledge base may include data from other analyses. For example, the recommendation platform may use the knowledge base to perform machine learning, data analysis, etc., to improve analysis of the process and/or operations.

In this way, implementations described herein increase an efficiency of analyzing a process of a healthcare organization and/or operations of the healthcare organization. In addition, the implementations improve an accuracy of a result and/or output of a process (e.g., by reducing a related deficiency), thereby conserving processing resources that would otherwise be consumed due to inaccurate results and/or outputs. Further, the implementations improve performance of a process and/or operations of a healthcare organization, thereby conserving processing resources and/or computing resources of devices used to implement the process and/or the operations.

Implementations will be described in the context of a healthcare organization. These implementations equally apply to other kinds of organizations, such as organizations relating to manufacturing, construction, information technology, or the like.

As indicated above, FIGS. 1A-1D are provided merely as an example. Other examples are possible and may differ from what was described with regard to FIGS. 1A-1D.

Figure 2:
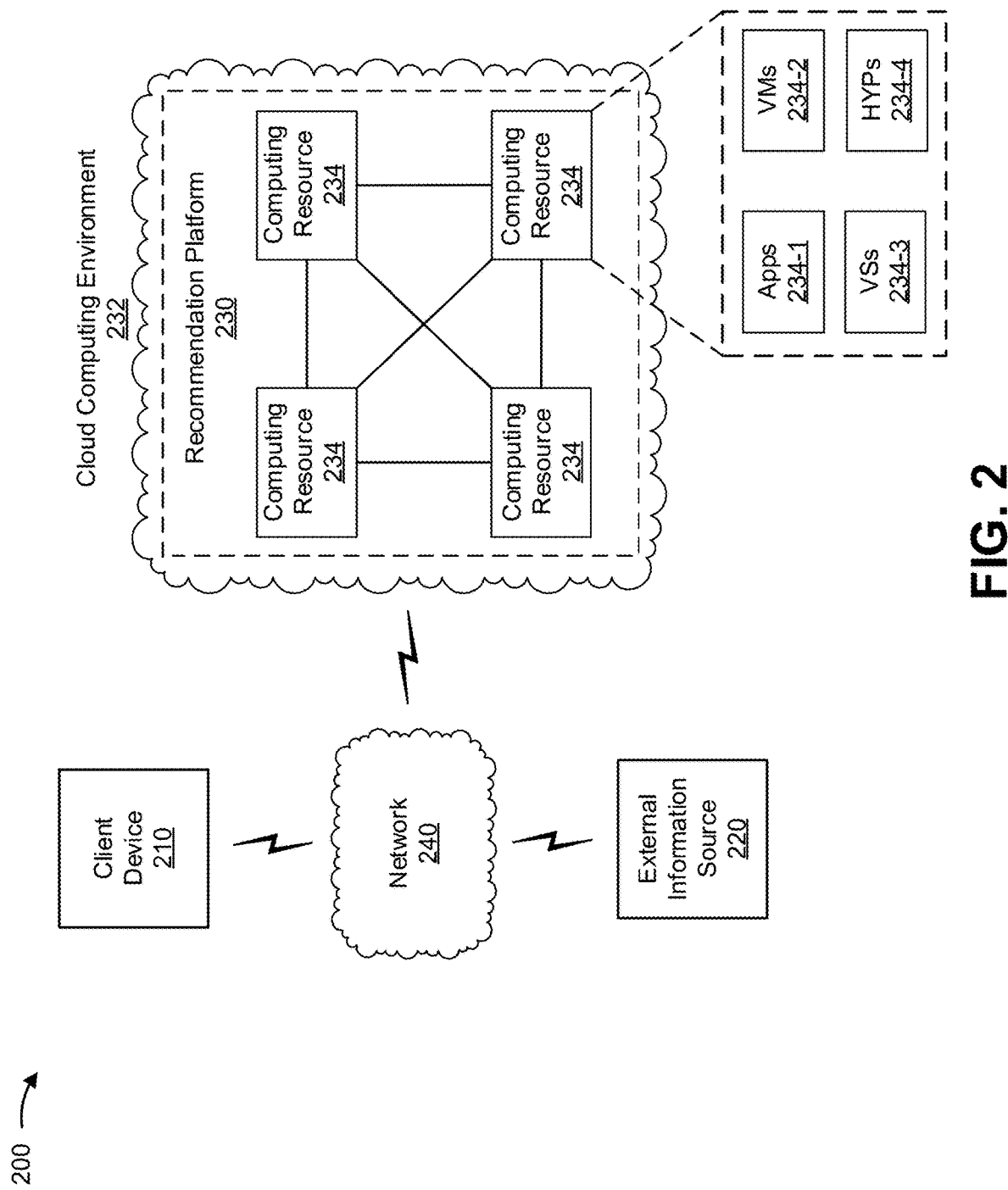
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include client device 210, external information source 220, recommendation platform 230, cloud computing environment 232, and a set of computing resources 234. Devices of environment 200 may interconnect via wired connections, wireless connections, or a combination of wired and wireless connections.

Client device 210 includes one or more devices capable of receiving, generating, storing, processing, and/or providing information associated with analyzing data related to integrated delivery and/or accountable care. For example, client device 210 may include a desktop computer, a mobile phone (e.g., a smart phone or a radiotelephone), a laptop computer, a tablet computer, a gaming device, a wearable communication device (e.g., a smart wristwatch or a pair of smart eyeglasses), or a similar type of device. In some implementations, client device 210 may receive data associated with an analysis that recommendation platform 230 has performed, as described elsewhere herein. Additionally, or alternatively, client device 210 may provide information for display (e.g., information related to an analysis of data related to performance of integrated care and/or accountable care), as described elsewhere herein.

External information source 220 includes one or more devices capable of receiving, generating, storing, processing, and/or providing information associated with an analysis of integrated care and/or accountable care. For example, external information source 220 may include a server (e.g., in a data center or a cloud computing environment), a data center (e.g., a multi-server micro data center), a workstation computer, a virtual machine (VM) provided in a cloud computing environment, or a similar type of device. In some implementations, external information source 220 may provide, to recommendation platform 230, information related to performance of a process and/or operations of a healthcare organization, as described elsewhere herein. Additionally, or alternatively, external information source 220 may store information related to an analysis of a healthcare organization, as described elsewhere herein.

Recommendation platform 230 includes one or more devices capable of analyzing data related to a healthcare organization. For example, recommendation platform 230 may include a cloud server or a group of cloud servers. In some implementations, recommendation platform 230 may be designed to be modular such that certain software components can be swapped in or out depending on a particular need. As such, recommendation platform 230 may be easily and/or quickly reconfigured for different uses.

In some implementations, as shown, recommendation platform 230 may be hosted in cloud computing environment 232. Notably, while implementations described herein describe recommendation platform 230 as being hosted in cloud computing environment 232, in some implementations, recommendation platform 230 may not be cloud-based (i.e., may be implemented outside of a cloud computing environment) or may be partially cloud-based.

Cloud computing environment 232 includes an environment that hosts recommendation platform 230. Cloud computing environment 232 may provide computation, software, data access, storage, and/or other services that do not require end-user knowledge of a physical location and configuration of a system and/or a device that hosts recommendation platform 230. As shown, cloud computing environment 232 may include a group of computing resources 234 (referred to collectively as "computing resources 234" and individually as "computing resource 234").

Computing resource 234 includes one or more personal computers, workstation computers, server devices, or another type of computation and/or communication device. In some implementations, computing resource 234 may host recommendation platform 230. The cloud resources may include compute instances executing in computing resource 234, storage devices provided in computing resource 234, data transfer devices provided by computing resource 234, etc. In some implementations, computing resource 234 may communicate with other computing resources 234 via wired connections, wireless connections, or a combination of wired and wireless connections.

As further shown in FIG. 2, computing resource 234 may include a group of cloud resources, such as one or more applications ("APPs") 234-1, one or more virtual machines ("VMs") 234-2, one or more virtualized storages ("VSs") 234-3, or one or more hypervisors ("HYPs") 234-4.

Application 234-1 includes one or more software applications that may be provided to or accessed by one or more devices of environment 200. Application 234-1 may eliminate a need to install and execute the software applications on devices of environment 200. For example, application 234-1 may include software associated with recommendation platform 230 and/or any other software capable of being provided via cloud computing environment 232. In some implementations, one application 234-1 may send/receive information to/from one or more other applications 234-1, via virtual machine 234-2.

Virtual machine 234-2 includes a software implementation of a machine (e.g., a computer) that executes programs like a physical machine. Virtual machine 234-2 may be either a system virtual machine or a process virtual machine, depending upon use and degree of correspondence to any real machine by virtual machine 234-2. A system virtual machine may provide a complete system platform that supports execution of a complete operating system ("OS"). A process virtual machine may execute a single program, and may support a single process. In some implementations, virtual machine 234-2 may execute on behalf of a user (e.g., a user of client device 210), and may manage infrastructure of cloud computing environment 232, such as data management, synchronization, or long-duration data transfers.

Virtualized storage 234-3 includes one or more storage systems and/or one or more devices that use virtualization techniques within the storage systems or devices of computing resource 234. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 234-4 provides hardware virtualization techniques that allow multiple operating systems (e.g., "guest operating systems") to execute concurrently on a host computer, such as computing resource 234. Hypervisor 234-4 may present a virtual operating platform to the guest operating systems, and may manage the execution of the guest operating systems. Multiple instances of a variety of operating systems may share virtualized hardware resources.

Network 240 includes one or more wired and/or wireless networks. For example, network 240 may include a cellular network (e.g., a long-term evolution (LTE) network, a code division multiple access (CDMA) network, a 3G network, a 4G network, a 5G network, or another type of cellular network), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
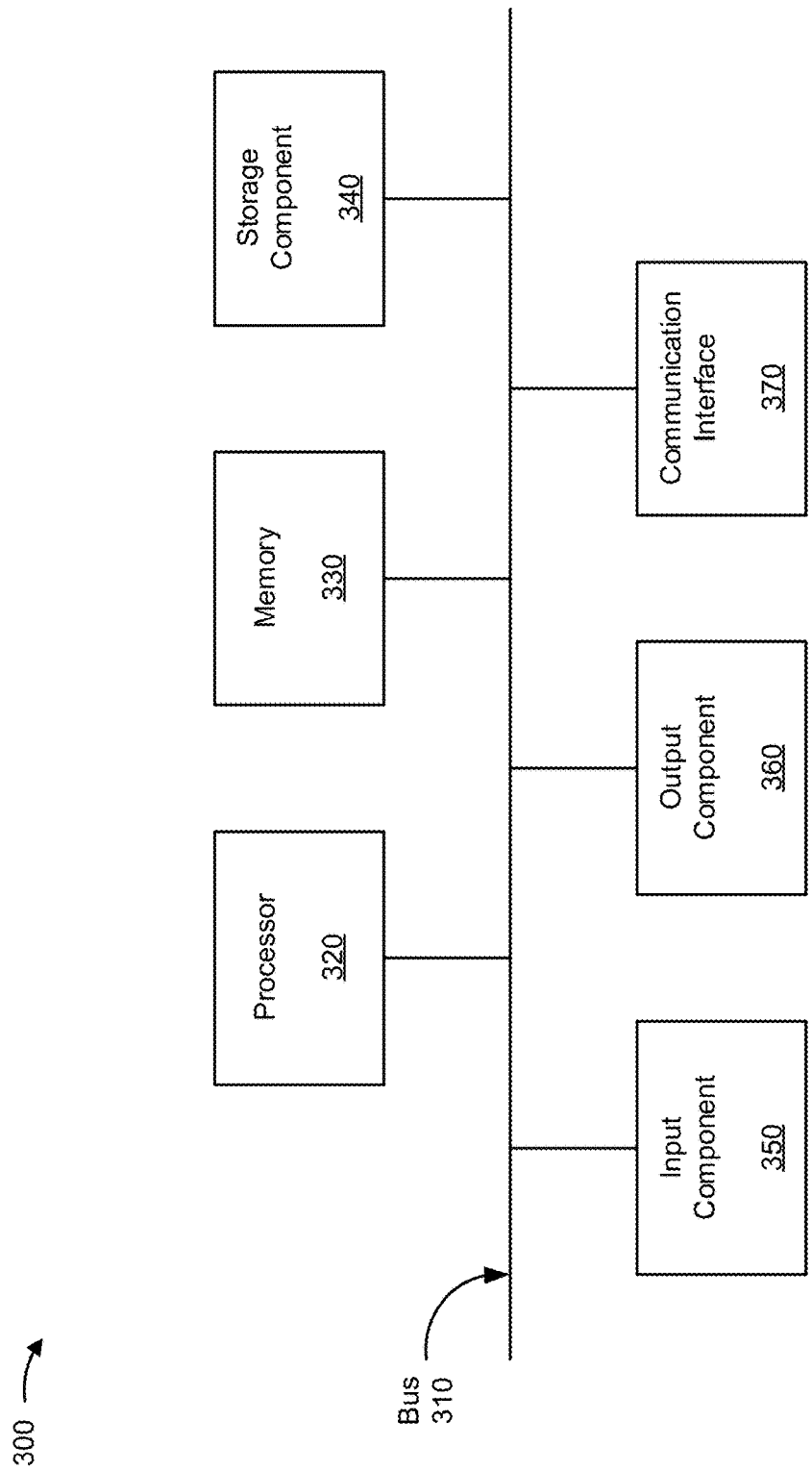
FIG. 3 is a diagram of example components of one or more devices of FIG. 2.

FIG. 3 is a diagram of example components of a device 300. Device 300 may correspond to client device 210, external information source 220, and/or recommendation platform 230. In some implementations, client device 210, external information source 220, and/or recommendation platform 230 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 includes a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operations and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
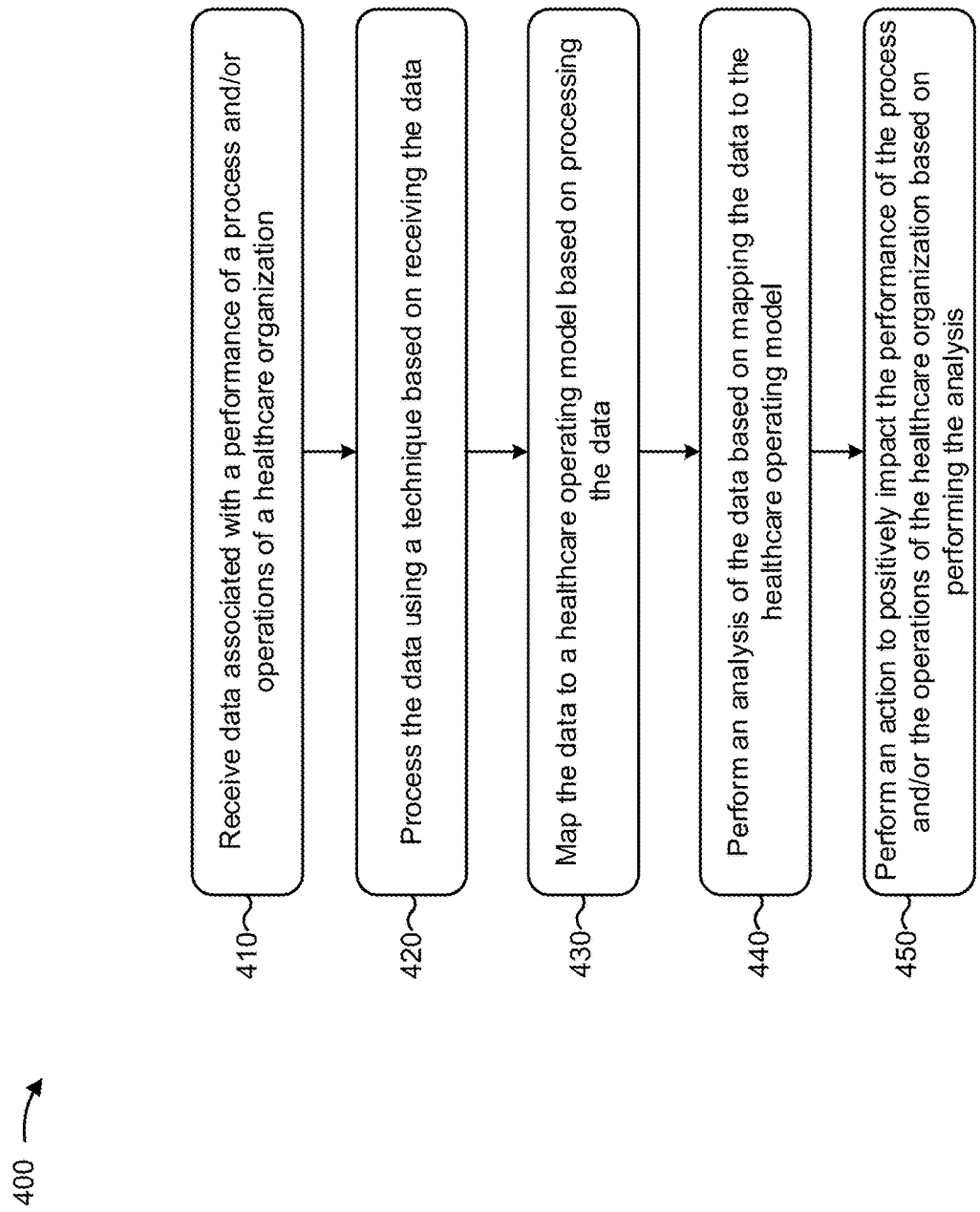
FIG. 4 is a flow chart of an example process for automatic analysis of organization process/operations data.

FIG. 4 is a flow chart of an example process 400 for automatic analysis of healthcare process/operations data. In some implementations, one or more process blocks of FIG. 4 may be performed by recommendation platform 230. In some implementations, one or more process blocks of FIG. 4 may be performed by another device or a group of devices separate from or including recommendation platform 230, such as client device 210 and external information source 220.

As shown in FIG. 4, process 400 may include receiving data associated with a performance of a process and/or operations of a healthcare organization (block 410). For example, recommendation platform 230 may receive data associated with a performance of a process and/or operations of a healthcare organization. In some implementations, recommendation platform 230 may receive the data periodically, according to a schedule, based on input from a user of client device 210, based on requesting the data, and/or the like. In some implementations, recommendation platform 230 may receive the data from external information source 220.

In some implementations, the data may relate to a healthcare organization. For example, the data may relate to an accountable care organization (e.g., a healthcare organization that provides coordinated care to a patient from doctors, hospitals, and other healthcare providers). Additionally, or alternatively, and as another example, the data may relate to a provider and/or integrated delivery organization (e.g., an organization that provides integrated diagnosis, treatment, management, etc., services for patients).

In some implementations, the data may relate to a performance of a process of the healthcare organization and/or operations of the healthcare organization. In some implementations, the data may relate to a value received and/or expended by the healthcare organization (e.g., related to providing a service to a patient). Additionally, or alternatively, the data may relate to a manner in which the organization has implemented the process. For example, the data may include data elements that identify a quantity of people associated with performance of a process, departments and/or functional areas of the healthcare organization related to the process, computing/processing/memory resources associated with implementation of the process, and/or the like.

Additionally, or alternatively, the data may relate to a manner in which a patient interacts with the healthcare organization. For example, the data may relate to, or identify, the systems with which the patient interacts when interacting with the organization, such as a quantity and/or type of systems with which the patient interacts, processing and/or computing resources that the systems consume during a patient interaction, and/or the like. Additionally, or alternatively, and as another example, the data may relate to a manner in which a patient call is handled (e.g., by a customer support center), a manner in which error tickets generated during a patient interaction are handled, and/or the like.

Additionally, or alternatively, the data may relate to metrics associated with the process and/or the operations of the healthcare organization. For example, the metrics may include a quantity of patients serviced by the healthcare organization, quantity and/or types of services provided to a patient, medical information related to a patient, errors related to processing patient information, an amount of time, processing resources, and/or computing resources used to implement a process and/or perform operations of the healthcare organization, and/or the like.

In some implementations, the data may include text (e.g., text from patient data records, registration forms, organization charts, consumer surveys, etc.), audio data, and/or video data. In some implementations, recommendation platform 230 may receive the data in a file. For example, recommendation platform 230 may receive the data in a comma separated values (CSV) file, a spreadsheet file, a text file, and/or the like. In this way, recommendation platform 230 may receive various types of files. In some implementations, recommendation platform 230 may receive millions, billions, or trillions of data elements when receiving the data.

In some implementations, recommendation platform 230 may store the data. For example, recommendation platform 230 may store the data using memory resources associated with recommendation platform 230. In some implementations, when storing the data, recommendation platform 230 may aggregate and/or merge the data with other data, deduplicate the data, and/or identify missing or corrupted data and obtain replacement data (e.g., using information related to the data, querying data from external information source 220, cross-referencing the data to identify the missing/corrupted data, and/or the like). This conserves memory resources of recommendation platform 230 and/or conserves processing resources of recommendation platform 230 by reducing errors in the data, reducing duplicate data, and/or the like. In some implementations, recommendation platform 230 may use a big data tool to aggregate and/or merge the data (e.g., to aggregate and/or merge millions, billions, trillions, etc., of data elements). In this way, recommendation platform 230 may receive a data set that cannot be received and/or processed manually, thereby increasing an efficiency of receiving data related to a healthcare organization.

In this way, recommendation platform 230 may receive data associated with a performance of a process and/or operations of a healthcare organization.

As further shown in FIG. 4, process 400 may include processing the data using a technique based on receiving the data (block 420). For example, recommendation platform 230 may process the data using a technique. In some implementations, recommendation platform 230 may process millions, billions, trillions, etc. of data elements when processing the data. In this way, recommendation platform 230 may process a data set that cannot be processed manually.

In some implementations, the technique may include natural language processing, text analysis, computational linguistics, and/or or the like. In some implementations, when processing the data using natural language processing, recommendation platform 230 may process the data to identify a term included in the data. For example, recommendation platform 230 may adjust characters (e.g., add characters, remove characters, etc.), adjust spacing in the data (e.g., add or remove spaces), expand acronyms included in the data (e.g., replace "EPA" with "Environmental Protection Agency"), replace a symbol with a term (e.g., replace an "@" symbol with the term "at"), convert a term included in the data to a root term (e.g., convert "processing," "processed," or "processor" to "process"), and/or the like.

Additionally, or alternatively, the technique may include pattern recognition, trend analysis, and/or the like. For example, recommendation platform 230 may use a big data tool to process millions, billions, and/or trillions of data elements to identify previously unidentifiable relationships and/or trends among data elements of the data, such as to identify a deficiency related to the data, to identify a manner in which to positively impact a deficiency, and/or the like.

Additionally, or alternatively, the technique may include automatic speech recognition (ASR), computer speech recognition, speech-to-text, and/or the like. For example, recommendation platform 230 may convert audio from an interview or customer support call to text. In some implementations, recommendation platform 230 may process a file associated with the data. In some implementations, recommendation platform 230 may process multiple file types. This improves performance of recommendation platform 230 by permitting recommendation platform 230 to receive files of various types (e.g., relative to receiving a single type of file).

In some implementations, recommendation platform 230 may process the data to identify metadata associated with the data (e.g., an identifier associated with the data that identifies a process with which the data is associated, a timestamp associated with the data, etc.). For example, recommendation platform 230 may process the data to identify a process with which the data is associated, a functional area of the healthcare organization with which the data is associated, operations of the healthcare organization with which the data is associated, and/or the like. This permits recommendation platform 230 to quickly and efficiently identify metadata associated with the data, thereby conserving processing resources of recommendation platform 230.

In some implementations, recommendation platform 230 may process the data to permit analysis of the data. For example, by processing the data, recommendation platform 230 may reduce errors associated with the data, may format the data such that recommendation platform 230 can map the data to an operating model (as described below), may normalize the data to permit inter-organization comparisons, and/or the like. This conserves processing resources of recommendation platform 230 and improves analyses using the data relative to using unprocessed data.

In this way, recommendation platform 230 may process the data using a technique based on receiving the data.

As further shown in FIG. 4, process 400 may include mapping the data to a healthcare operating model based on processing the data (block 430). For example, recommendation platform 230 may map the data to a healthcare operating model based on processing the data. In some implementations, the healthcare operating model may include a model that identifies an area of a healthcare organization (e.g., a functional area and/or a sub-area of a functional area that the healthcare organization uses to implement a process and/or operations).

In some implementations, the healthcare operating model may be based on analyses of other organizations. For example, the healthcare operating model may represent a benchmark structure and/or organizational structure of another healthcare organization (e.g., a healthcare organization identified as a high-performing healthcare organization), an industry standard, and/or the like. In some implementations, recommendation platform 230 may use the operating model to identify a rule (e.g., related to data, a functional area, or a sub-area), a threshold related to data, an industry standard, a metric related to a process and/or operations of a healthcare organization, and/or the like to apply to data related to a process and/or operations of a healthcare organization when analyzing the data. This permits recommendation platform 230 to quickly identify a rule, a threshold, a metric, and/or the like by mapping data to a healthcare operating model.

In some implementations, the healthcare operating model may be based on a type of healthcare organization being analyzed. For example, recommendation platform 230 may use an accountable care operating model for an accountable care organization, a provider and/or integrated delivery operating model for a provider and/or integrated delivery organization, and/or the like. Additionally, or alternatively, the healthcare operating model may be based on a type of analysis being performed. For example, the healthcare operating model may include functional areas and/or sub-areas specific to analyzing values of a healthcare organization when analyzing values associated with a healthcare organization.

In some implementations, recommendation platform 230 may map the data to an area and/or a sub-area of the healthcare operating model. In some implementations, recommendation platform 230 may map the data based on an identifier associated with the data (e.g., an identifier that identifies a functional area with which the data is associated). This conserves processing resources of recommendation platform 230 via quick and efficient mapping of the data. Additionally, or alternatively, recommendation platform 230 may map the data based on a type of the data (e.g., when the functional areas of the healthcare organization do not match the functional areas of the healthcare operating model). For example, recommendation platform 230 may map the data based on previous mappings, using artificial intelligence, and/or the like. This improves mapping of the data by permitting recommendation platform 230 to map data when functional areas of the healthcare organization being analyzed do not match functional areas of the healthcare operating model (e.g., relative to a device that cannot map data when functional areas or sub-areas of a healthcare organization do not match functional areas or sub-areas of a healthcare operating model).

In some implementations, recommendation platform 230 may map the data to permit analysis of the data. For example, recommendation platform 230 may map the data to permit a comparison of a process implemented by the healthcare organization and another healthcare organization identified as a high performing healthcare organization, to identify a deficiency related to a process and/or operations of the healthcare organization, and/or the like, as described in more detail elsewhere herein.

In some implementations, recommendation platform 230 may generate the healthcare operating model prior to mapping the data. For example, recommendation platform 230 may receive data associated with other healthcare organizations (e.g., different from the healthcare organization that recommendation platform 230 is analyzing) and may generate the healthcare operating model based on the received data. Continuing with the previous example, recommendation platform 230 may generate a healthcare operating model that identifies functional areas, or sub-areas, of the other healthcare organizations based on the received data (e.g., data that identifies functional areas and/or sub-areas of the other healthcare organizations, a manner in which the other healthcare organizations implement a process and/or operations, etc.). In this way, recommendation platform 230 may generate a healthcare operating model.

In this way, recommendation platform 230 may map the data to a healthcare operating model based on processing the data.

As further shown in FIG. 4, process 400 may include performing an analysis of the data based on mapping the data to the healthcare operating model (block 440). For example, recommendation platform 230 may perform an analysis of the data based on mapping the data to the healthcare operating model. In some implementations, recommendation platform 230 may use a metric, a rule, data related to a process and/or operations of another healthcare organization (e.g., a high performing healthcare organization), and/or the like identified by a healthcare operating model to perform the analysis. For example, when recommendation platform 230 maps data to the healthcare operating model, recommendation platform 230 may identify a metric, a rule, other data, and/or the like associated with a functional area and/or a sub-area of the operating model to which the data was mapped. Continuing with the previous example, recommendation platform 230 may use the identified metric, rule, data, and/or the like to perform the analysis.

In some implementations, recommendation platform 230 may perform the analysis to identify a deficiency related to a process implemented by a healthcare organization and/or a manner in which to improve operations of the healthcare organization. In some implementations, recommendation platform 230 may identify a deficiency when a metric does not satisfy a threshold, satisfies a first threshold rather than a second threshold, fails to satisfy a threshold by a threshold amount, and/or the like. Additionally, or alternatively, recommendation platform 230 may compare functional areas of a healthcare organization and a healthcare operating model and may identify a deficiency when the healthcare organization is missing a functional area or a sub-area included in the healthcare operating model (e.g., the functional areas of the healthcare organization and the healthcare operating model do not match). Additionally, or alternatively, recommendation platform 230 may identify a deficiency related to volume, storage capacity, and/or processing capabilities of computer hardware and/or electronic devices utilized in performing a process and/or operations of the healthcare organization.

In some implementations, recommendation platform 230 may identify a deficiency and/or a manner in which to improve a healthcare organization by comparing functional areas of the healthcare organization that are used to implement a process and functional areas of another healthcare organization (e.g., by using the healthcare operating model), and may determine that the functional areas used are different. In this case, recommendation platform 230 may identify a deficiency and/or a manner in which to improve the operations of a healthcare organization by identifying functional areas that the healthcare organization can use to implement a process and that are different than the functional areas that the healthcare organization is using.

Additionally, or alternatively, recommendation platform 230 may identify a deficiency and/or a manner in which to improve an organization by identifying a potentially inefficient combination of functional areas or sub-areas used to implement a process. For example, recommendation platform 230 may identify the potentially inefficient combination of functional areas or sub-areas based on previous analyses that identified an inefficient combination of functional areas, using machine learning, using pattern recognition, and/or the like. In this case, recommendation platform 230 may identify a deficiency and/or a manner in which to improve operations of the healthcare organization by identifying a more efficient combination of functional areas and/or sub-areas to use to implement a process and/or operations, thereby conserving processing resources related to implementing the process and/or operations.

Additionally, or alternatively, recommendation platform 230 may identify a deficiency and/or a manner in which to improve a healthcare organization by identifying a threshold quantity of functional areas or sub-areas that the healthcare organization uses to implement the process and/or operations. For example, the threshold quantity may indicate a complex implementation of a process and/or operations, thereby reducing efficiency of the operations of the organization. In this way, recommendation platform 230 may identify a deficiency and/or a manner in which to improve a process and/or operations of the healthcare organization by identifying a more efficient combination of functional areas and/or sub-areas to use to implement a process and/or operations. Additionally, or alternatively, recommendation platform 230 may identify a deficiency and/or a manner in which to improve the healthcare organization by determining that volume, storage capacity, and/or processing capabilities of computer hardware and/or electronic devices utilized in performing a process and/or operations of the healthcare organization do not satisfy a threshold, satisfy a threshold, satisfy a first threshold but not a second threshold, and/or the like. This conserves processing resources related to implementation of a process and/or operations, improves an efficiency of a process and/or operations, and/or the like.

In some implementations, recommendation platform 230 may generate a score related to an identified deficiency. For example, the score may relate to a severity of an inefficiency, resources and/or expenses associated with fixing an identified deficiency or with improving operations, a priority of the deficiency (e.g., for fixing the deficiency), a priority of improving the operations, and/or the like. In this way, recommendation platform 230 may quickly and efficiently prioritize deficiencies and determine a severity of a first deficiency relative to a second deficiency.

In some implementations, recommendation platform 230 may store a result of the analysis in a knowledge base or knowledge graph. For example, recommendation platform 230 may aggregate the data with information for results of other analyses. In some implementations, recommendation platform 230 may use the knowledge base to perform machine learning to improve future analyses of the same or a different healthcare organization, to perform a big data analysis, and/or the like. In some implementations, a knowledge base or knowledge graph may include technology used to store complex structured and unstructured data used by a computer system.

In this way, recommendation platform 230 may perform an analysis of the data based on mapping the data to a healthcare operating model.

As further shown in FIG. 4, process 400 may include performing an action to positively impact the performance of the process and/or the operations of the healthcare organization based on performing the analysis (block 450). For example, recommendation platform 230 may perform an action to positively impact the performance of the process and/or the operations of the healthcare organization based on performing the analysis. In some implementations, a positive impact may occur when an action causes a desired result or action to be achieved. Additionally, or alternatively, a positive impact may occur when an action increases the likelihood that a desired result of an action will be achieved.

In some implementations, recommendation platform 230 may generate a recommendation. For example, recommendation platform 230 may generate a recommendation to use different functional areas to implement a process and/or operations, a recommendation to use different systems to implement a process and/or operations (e.g., to consolidate systems), a recommendation to use different sub-areas to implement a process and/or operations, a recommendation to add a process and/or operations associated with a functional area or sub-area, a recommendation to remove a process and/or operations associated with a functional area or sub-area, and/or the like.

In some implementations, recommendation platform 230 may generate the recommendation using information related to the analysis. For example, recommendation platform 230 may generate a recommendation to fix a particular deficiency identified during an analysis. In some implementations, recommendation platform 230 may generate multiple recommendations.

In some implementations, recommendation platform 230 may generate a score for each of the multiple recommendations. For example, recommendation platform 230 may generate a score based on a predicted impact of the recommendation (e.g., as determined using data from prior analyses and prior implemented recommendations).

In some implementations, recommendation platform 230 may provide information identifying a recommendation to a device to cause the device to implement the recommendation based on a score for the recommendation. For example, recommendation platform 230 may provide information identifying a recommendation that has the highest score relative to other scores for other recommendations, that has a threshold score, and/or the like. In this way, recommendation platform 230 may optimize providing recommendations to a device that implements a process and/or operations of a healthcare organization, thereby increasing an efficiency of providing recommendations and/or conserving processing resources of recommendation platform 230 (e.g., relative to providing all recommendations, providing a recommendation that may fail to have a predicted result, etc.).

In some implementations, recommendation platform 230 may send a message (e.g., an email or a short message service (SMS) message) to client device 210. For example, the message may include information related to the analysis and/or a generated recommendation. In some implementations, recommendation platform 230 may schedule a meeting (e.g., to discuss the analysis or a generated recommendation). For example, recommendation platform 230 may schedule a meeting using electronic calendars of individuals associated with the healthcare organization to identify an available time for the meeting.

In some implementations, recommendation platform 230 may send a set of instructions to modify a manner in which devices implement a process and/or operations. For example, recommendation platform 230 may send a set of instructions to modify which systems and/or devices are used to implement a process (e.g., to reduce or increase a quantity of systems used). In this way, recommendation platform 230 may modify a manner in which a system and/or device implements a process and/or operations.

In some implementations, recommendation platform 230 may manage implementation of a process and/or operations. For example, recommendation platform 230 may track metrics associated with implementation of a process and/or operations, may perform an analysis (e.g., of the metrics) to determine a more efficient manner of performing the process and/or operations, and/or the like. In this case, recommendation platform 230 may send a set of instructions (e.g., to client device 210) when recommendation platform 230 identifies a more efficient manner for implementing the process and/or operations.

In some implementations, recommendation platform 230 may provide information for an analysis to another recommendation platform 230. For example, recommendation platform 230 may provide the information to improve future analyses of the other recommendation platform 230. This improves an accuracy of an analysis of the other recommendation platform 230, thereby conserving processing resources that would otherwise be consumed due to an inaccurate or inefficient analysis.

In some implementations, recommendation platform 230 may monitor post-recommendation actions, such as to determine whether an impact of an action matches a predicted impact. For example, if recommendation platform 230 generates a recommendation to reduce a quantity of devices used to implement a process, recommendation platform 230 may monitor the process to determine whether the devices that are implementing the process use fewer processing resources after the quantity of devices is reduced. This improves implementation of a recommendation by preventing a device from implementing an ineffective recommendation.

In some implementations, recommendation platform 230 may bring a device and/or software online or offline. For example, recommendation platform 230 may send a set of instructions to a device, install and/or activate software on a device, and/or the like. Additionally, or alternatively, recommendation platform 230 may update software installed on a device. Additionally, or alternatively, recommendation platform 230 may push software to a device, so as to update the software. In this way, recommendation platform 230 may improve functioning of a device via updating of software, adjusting whether the device is online or offline, and/or the like.

In some implementations, recommendation platform 230 may perform the actions described herein in real-time or near real-time. For example, recommendation platform 230 may analyze and modify a process and/or operations of a healthcare organization as the healthcare organization is implementing the process and/or the operations. This conserves processing resources of a device used to implement the process and/or operations by reducing an amount of time that the device implements a process and/or operations that include a deficiency (e.g., relative to delayed performance of an action).

In this way, recommendation platform 230 may perform an action to positively impact a performance of a process and/or operations of a healthcare organization based on performing an analysis.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

FIGS. 5A-5D are diagrams of an example implementation 500 relating to example process 400 shown in FIG. 4. FIGS. 5A-5D show an example of analyzing an individual interaction with a healthcare organization. As shown in FIGS. 5A-5D, example implementation 500 may include client devices 210, external information sources 220, and recommendation platform 230.

Figure 5A:
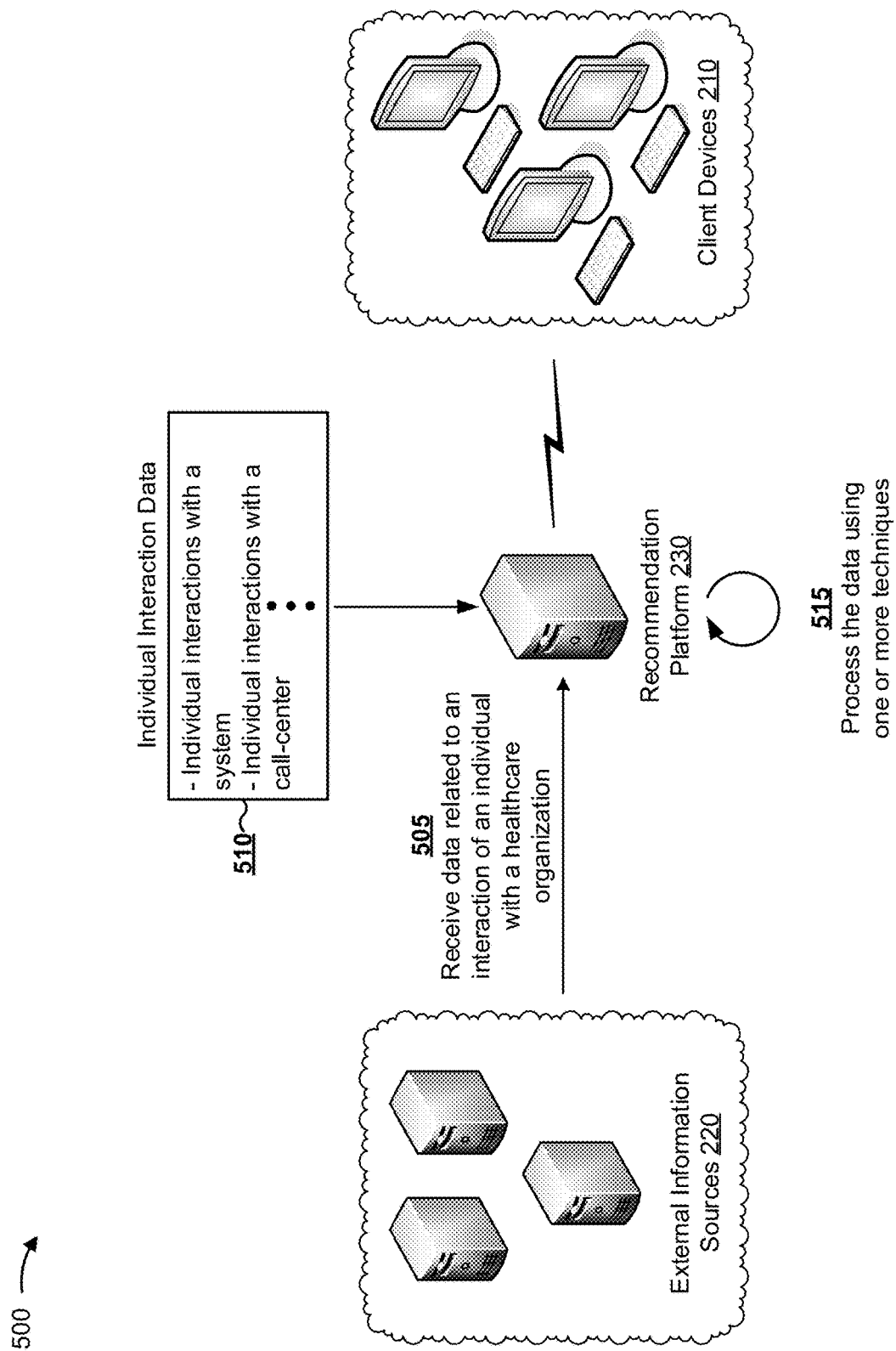
FIGS. 5A-5D are diagrams of an example implementation relating to the example process shown in FIG. 4.

As shown in FIG. 5A, and by reference number 505, recommendation platform 230 may receive data related to an interaction of an individual (e.g., a patient) with a healthcare organization (e.g., individual interaction data). For example, as shown by reference number 510, the individual interaction data may include data elements associated with individual interactions with a system, individual interactions with a call-center, and/or the like. As shown by reference number 515, recommendation platform 230 may process the data using one or more techniques (e.g., natural language processing, text analysis, computational linguistics, etc.), as described elsewhere herein.

Figure 5B:
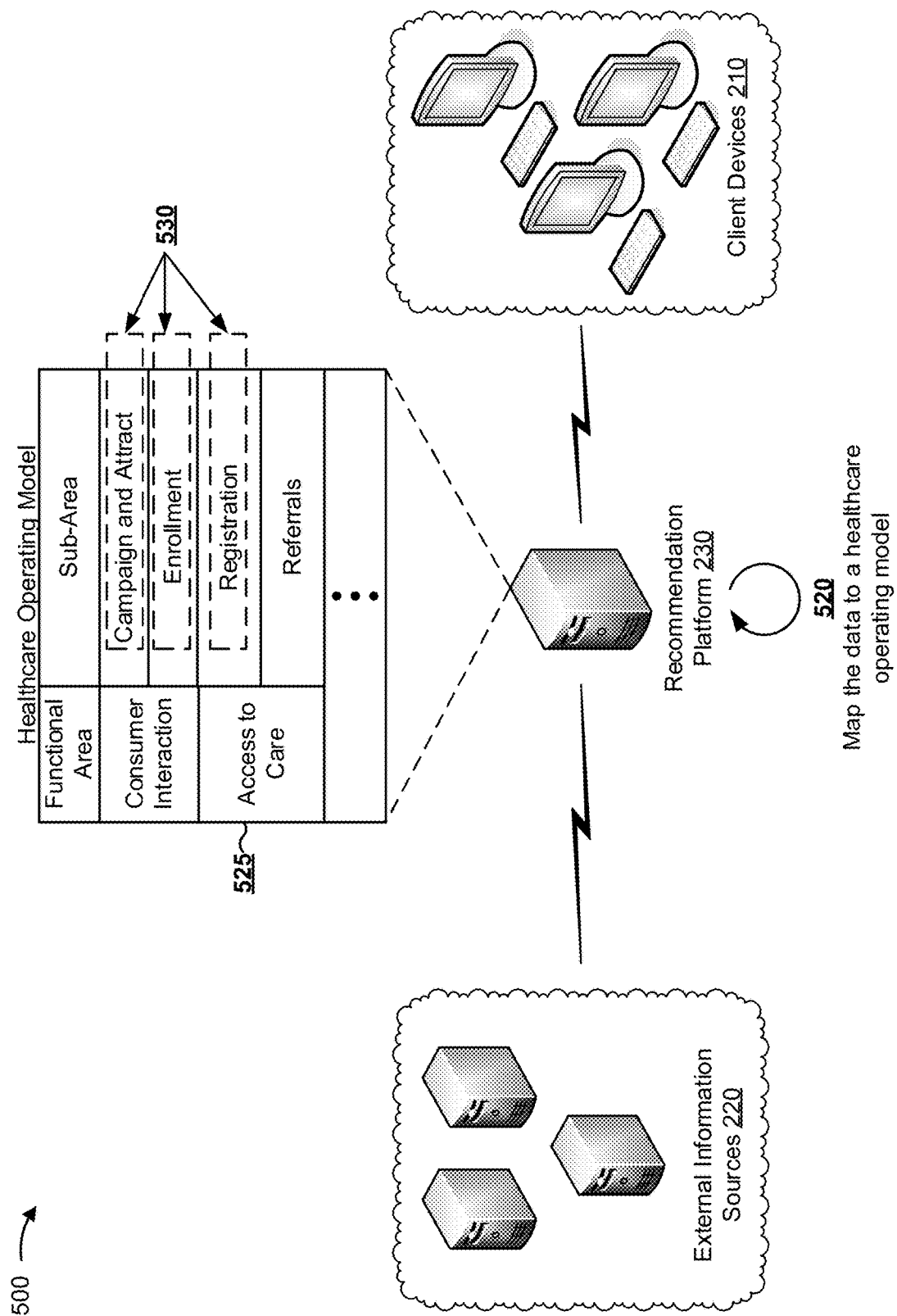

As shown in FIG. 5B, and by reference number 520, recommendation platform 230 may map the data to a healthcare operating model. For example, as shown by reference number 525, the healthcare operating model may include functional areas (e.g., consumer interaction and access to care) and each functional area may be associated with sub-areas (e.g., the consumer interaction functional area may be associated with campaign and attract and enrollment sub-areas, and the access to care functional area may be associated with registration and referrals sub-areas). As shown by reference number 530, recommendation platform 230 may map the data to sub-areas with which an individual interacts (e.g., campaign and attract, enrollment, and registration). In some implementations, the mapping may identify sub-areas that the healthcare organization uses to implement a process. For example, the data may map to a process that the healthcare organization uses to attract new patients, enroll the patients with the healthcare organization, and register the patients for healthcare services. In this way, recommendation platform 230 may determine a manner in which an individual interacts with a healthcare organization.

Figure 5C:
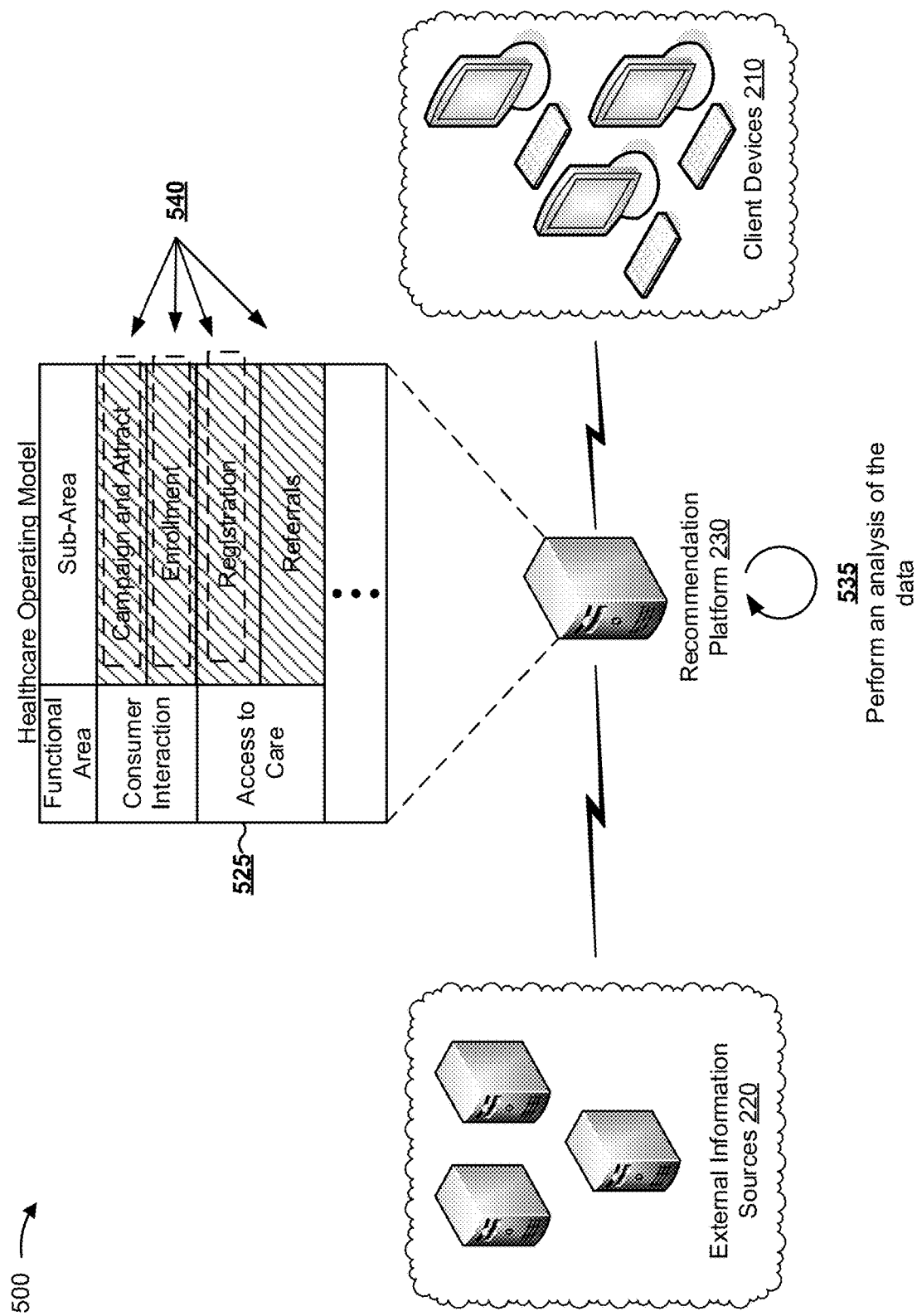

As shown in FIG. 5C, and by reference number 535, recommendation platform 230 may perform an analysis of the data. For example, recommendation platform 230 may determine whether an individual interacts with a threshold quantity of functional areas and/or sub-areas (or corresponding systems), whether an individual interacts with the same functional areas and/or sub-areas as an individual interacting with a different healthcare organization, and/or the like. As shown by reference number 540, recommendation platform 230 may identify differences between sub-areas of a healthcare operating model (e.g., representing a model healthcare organization or a high performing healthcare organization) used to implement a similar process, as indicated by striped boxes, and the sub-areas of that the healthcare organization being analyzed uses, as indicated by dotted lines. In this case, recommendation platform 230 may determine that the healthcare organization is not using a referrals sub-area to implement a process and that the healthcare organization can increase an efficiency of the process by including use of the referrals functional area when implementing the process (e.g., by incorporating functions of the referrals functional area into the process).

Figure 5D:
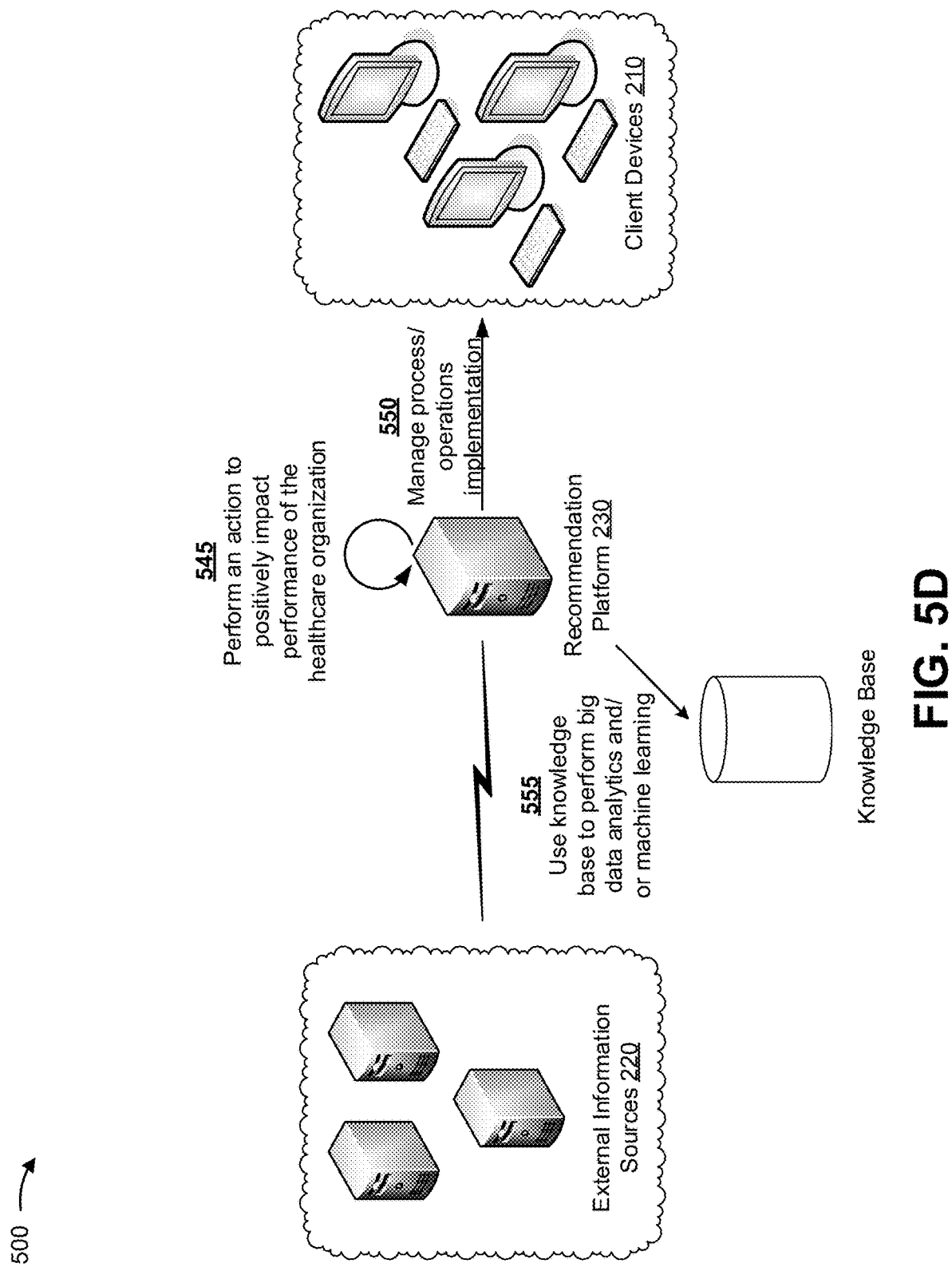

As shown in FIG. 5D, and by reference number 545, recommendation platform 230 may perform an action to positively impact performance of the healthcare organization (e.g., generate a recommendation, update software, push software to one or more devices associated with the healthcare organization, etc., to improve individual interaction). As shown by reference number 550, recommendation platform 230 may manage implementation of a process and/or operations (e.g., based on the analysis and/or action). As shown by reference number 555, recommendation platform 230 may use a knowledge base to perform big data analytics and/or machine learning using data from performing the analysis, managing process and/or operations implementation, and/or the like.

In some implementations, recommendation platform 230 may perform big data analytics to identify trends among multiple healthcare organizations, thereby enabling recommendation platform 230 to identify new and/or different deficiencies. Additionally, or alternatively, recommendation platform 230 may use machine learning to improve an accuracy of identifying a deficiency by using information related to identified deficiencies for multiple healthcare organizations.

As indicated above, FIGS. 5A-5D are provided merely as an example. Other examples are possible and may differ from what was described with regard to FIGS. 5A-5D.

FIGS. 6A-6D are diagrams of an example implementation 600 relating to example process 400 shown in FIG. 4. FIGS. 6A-6D show an example of analyzing a capability of a healthcare organization to perform new and different functions that the healthcare organization does not currently perform. As shown in FIGS. 6A-6D, example implementation 600 may include client devices 210, external information sources 220, and recommendation platform 230.

Figure 6A:
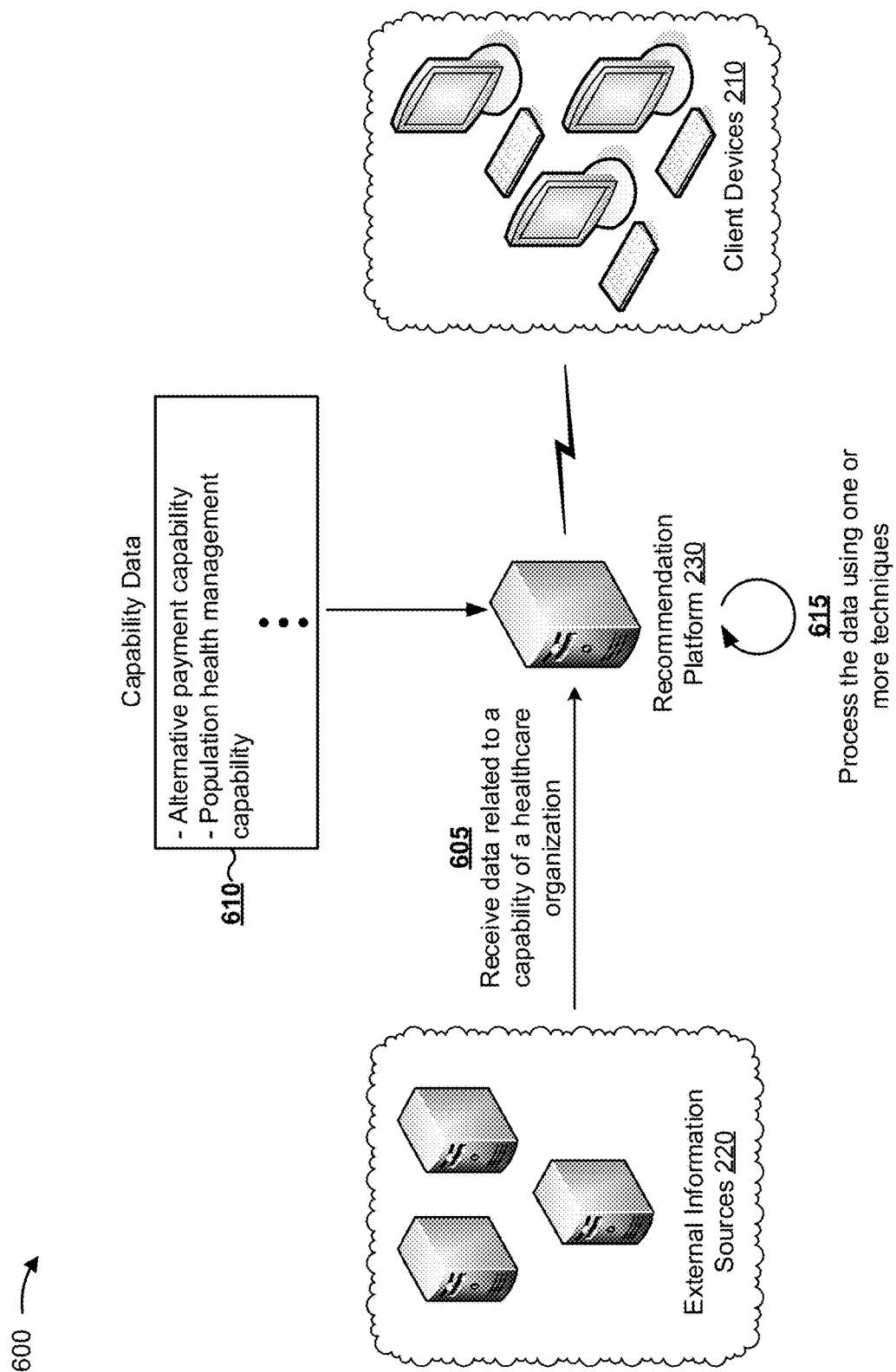
FIGS. 6A-6D are diagrams of an example implementation relating to the example process shown in FIG. 4.

As shown in FIG. 6A, and by reference number 605, recommendation platform 230 may receive data related to a capability of a healthcare organization (e.g., capability data). For example, as shown by reference number 610, the capability data may include data elements related to an alternative payment capability, data elements related to a population health management capability, and/or the like. As shown by reference number 615, recommendation platform 230 may process the data using one or more techniques, as described elsewhere herein.

Figure 6B:
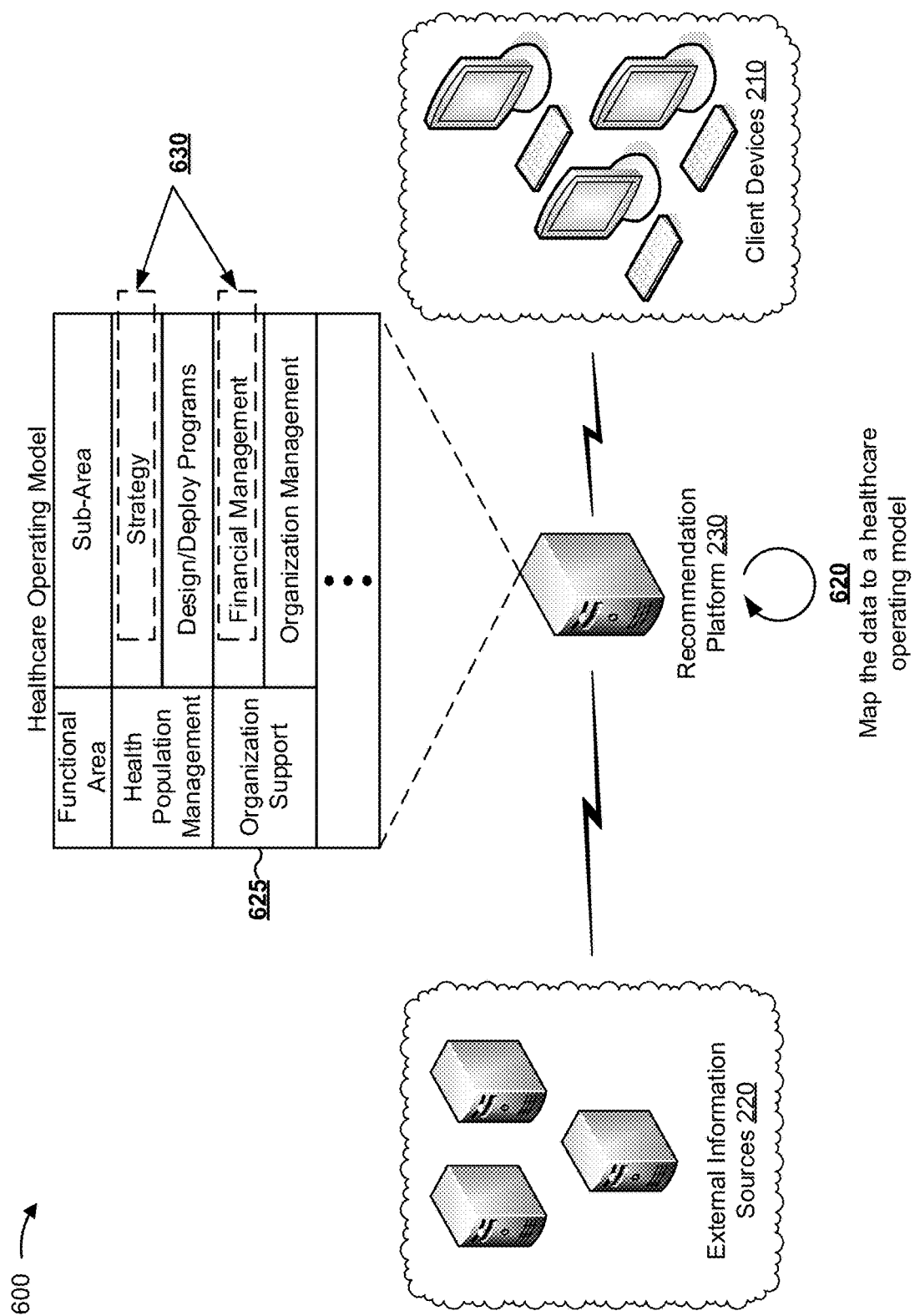

As shown in FIG. 6B, and by reference number 620, recommendation platform 230 may map the data to a healthcare operating model. For example, as shown by reference number 625, the healthcare operating model may include health population management as a functional area that includes strategy and design and/or deploy programs as sub-areas, and may include organization support as a functional area that includes financial management and organization management as sub-areas. As shown by reference number 630, recommendation platform 230 may map the information to sub-areas that relate to implementing particular capabilities of a healthcare organization (e.g., strategy and financial management). In some implementations, the mapping of the data may identify a capability that a healthcare organization can implement, a readiness of a healthcare organization to implement a capability, and/or the like.

Figure 6C:
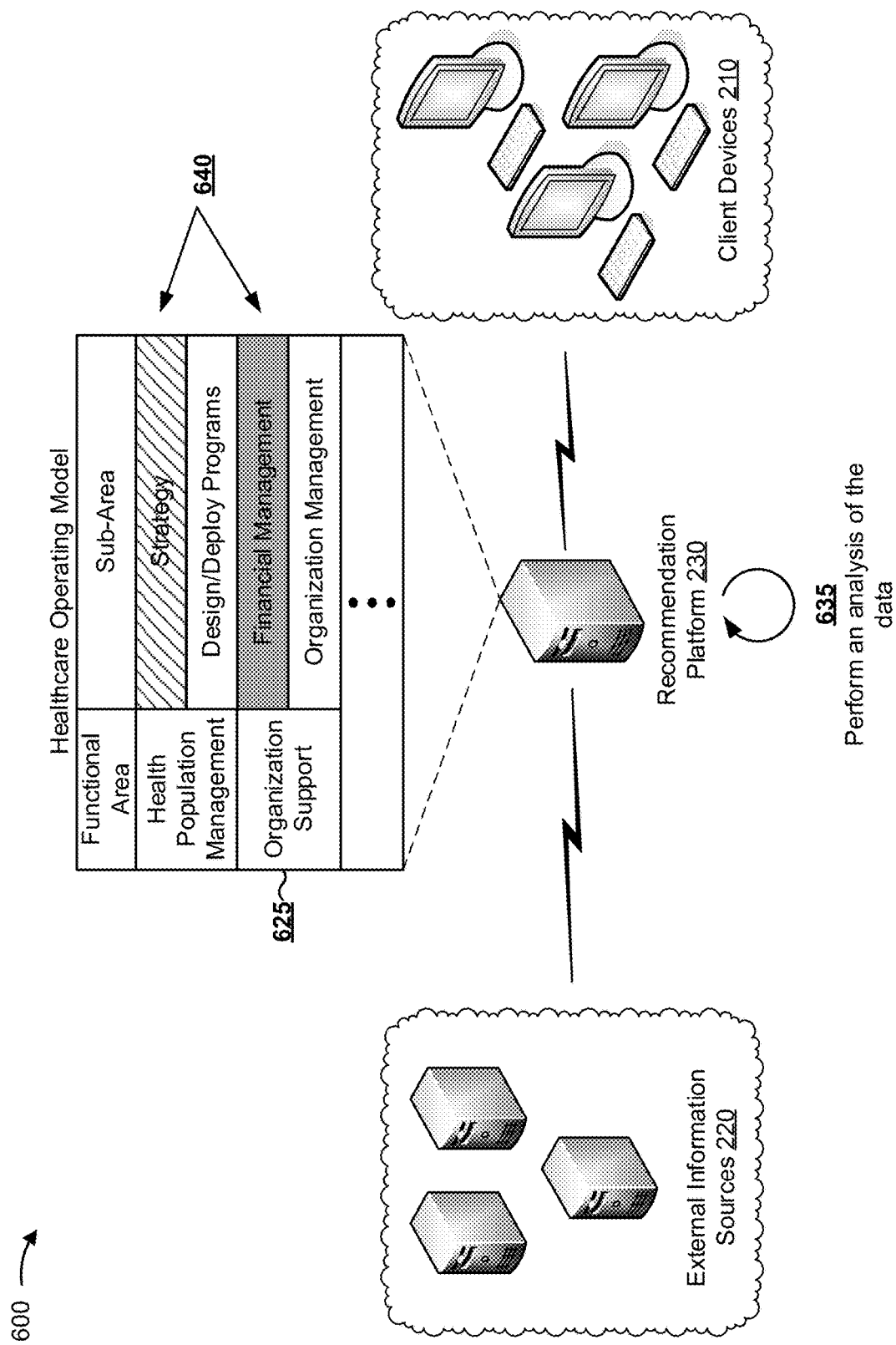

As shown in FIG. 6C, and by reference number 635, recommendation platform 230 may perform an analysis of the data. For example, recommendation platform 230 may compare data related to capabilities of the healthcare organization and the healthcare operating model to determine whether a healthcare organization has sufficient capabilities to perform particular functions. In some implementations, recommendation platform 230 may identify functional areas and/or sub-areas where the healthcare organization has sufficient capabilities, insufficient capabilities, capabilities that satisfy a threshold, a threshold readiness to perform a function related to a capability, and/or the like. In this case, as shown by reference number 640, recommendation platform 230 may identify a sub-area where a capability (e.g., financial management) is insufficiently implemented (e.g., does not satisfy a first threshold), shown as a shaded box, to perform a particular function related to a capability. In addition, as further shown by reference number 640, recommendation platform 230 may identify a sub-area where a capability (e.g., strategy) satisfies a first threshold but not a second threshold, shown as a striped box, indicating that the healthcare organization can perform some new functions related to a capability.

Figure 6D:
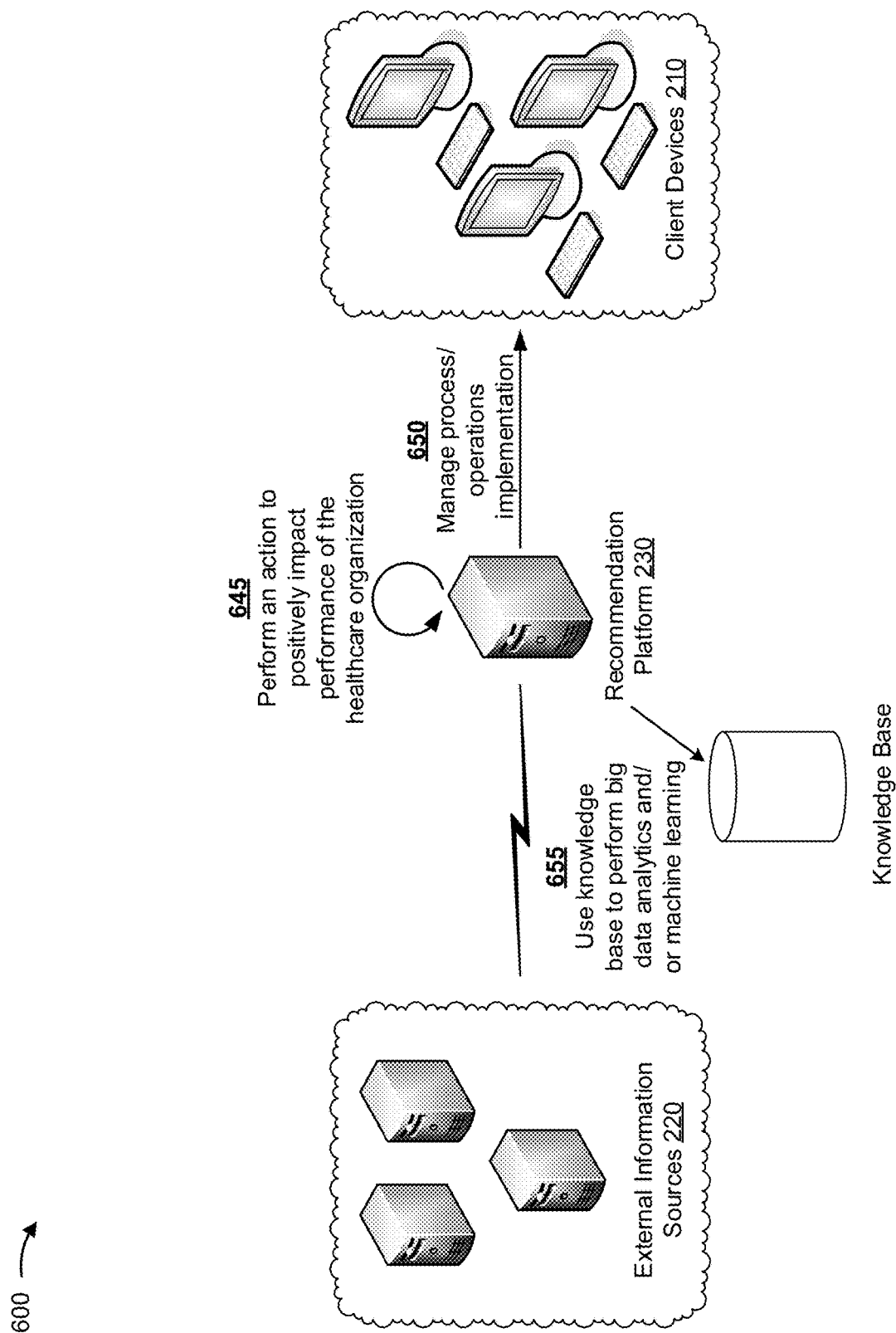

As shown in FIG. 6D, and by reference number 645, recommendation platform 230 may perform an action to positively impact performance of the healthcare organization (e.g., generate a recommendation, send a message, schedule a meeting, etc., to improve capabilities of the healthcare organization). As shown by reference number 650, recommendation platform 230 may manage implementation of a process and/or operations (e.g., based on the analysis and/or action). As shown by reference number 655, recommendation platform 230 may use a knowledge base to perform big data analytics and/or machine learning.

As indicated above, FIGS. 6A-6D are provided merely as an example. Other examples are possible and may differ from what was described with regard to FIGS. 6A-6D.

FIGS. 7A-7D are diagrams of an example implementation 700 relating to example process 400 shown in FIG. 4. FIGS. 7A-7D show an example of analyzing a reporting and/or compliance function of a healthcare organization. As shown in FIGS. 7A-7D, example implementation 700 may include client devices 210, external information sources 220, and recommendation platform 230.

Figure 7A:
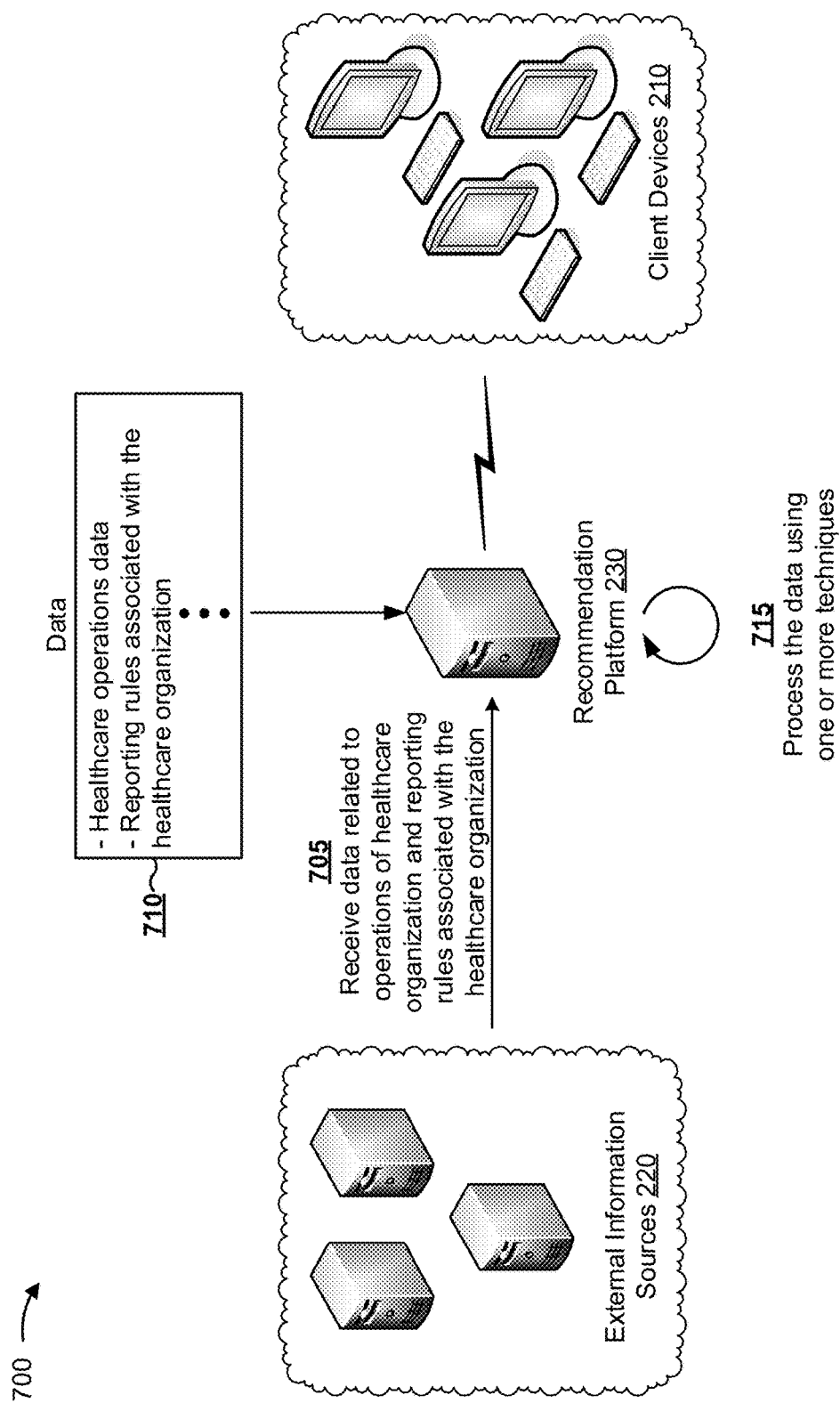
FIGS. 7A-7D are diagrams of an example implementation relating to the example process shown in FIG. 4.

As shown in FIG. 7A, and by reference number 705, recommendation platform 230 may receive data related to operations of a healthcare organization and reporting rules associated with the healthcare organization. For example, as shown by reference number 710, the data received may include healthcare operations data, data related to reporting rules associated with the healthcare organization, and/or the like. As shown by reference number 715, recommendation platform 230 may process the data using one or more techniques, as described elsewhere herein.

Figure 7B:
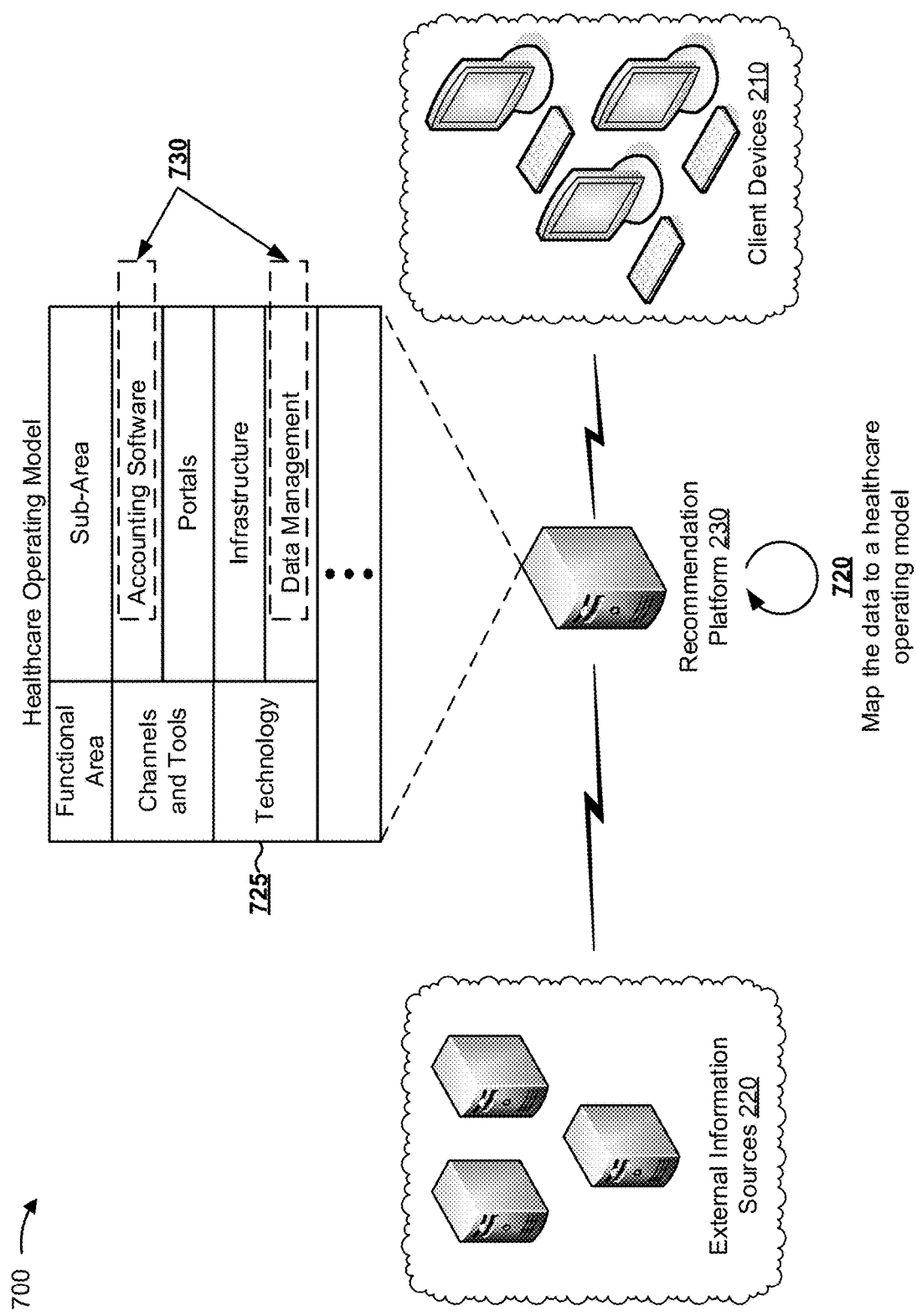

As shown in FIG. 7B, and by reference number 720, recommendation platform 230 may map the data to a healthcare operating model. For example, as shown by reference number 725, the healthcare operating model may include channels and tools as a functional area that includes accounting software and portals as sub-areas, and may include technology as a functional area that includes infrastructure and data management as sub-areas. As shown by reference number 730, recommendation platform 230 may map the data to sub-areas that perform reporting and/or compliance functions and/or that have reporting/compliance obligations (e.g., accounting software, data management).

Figure 7C:
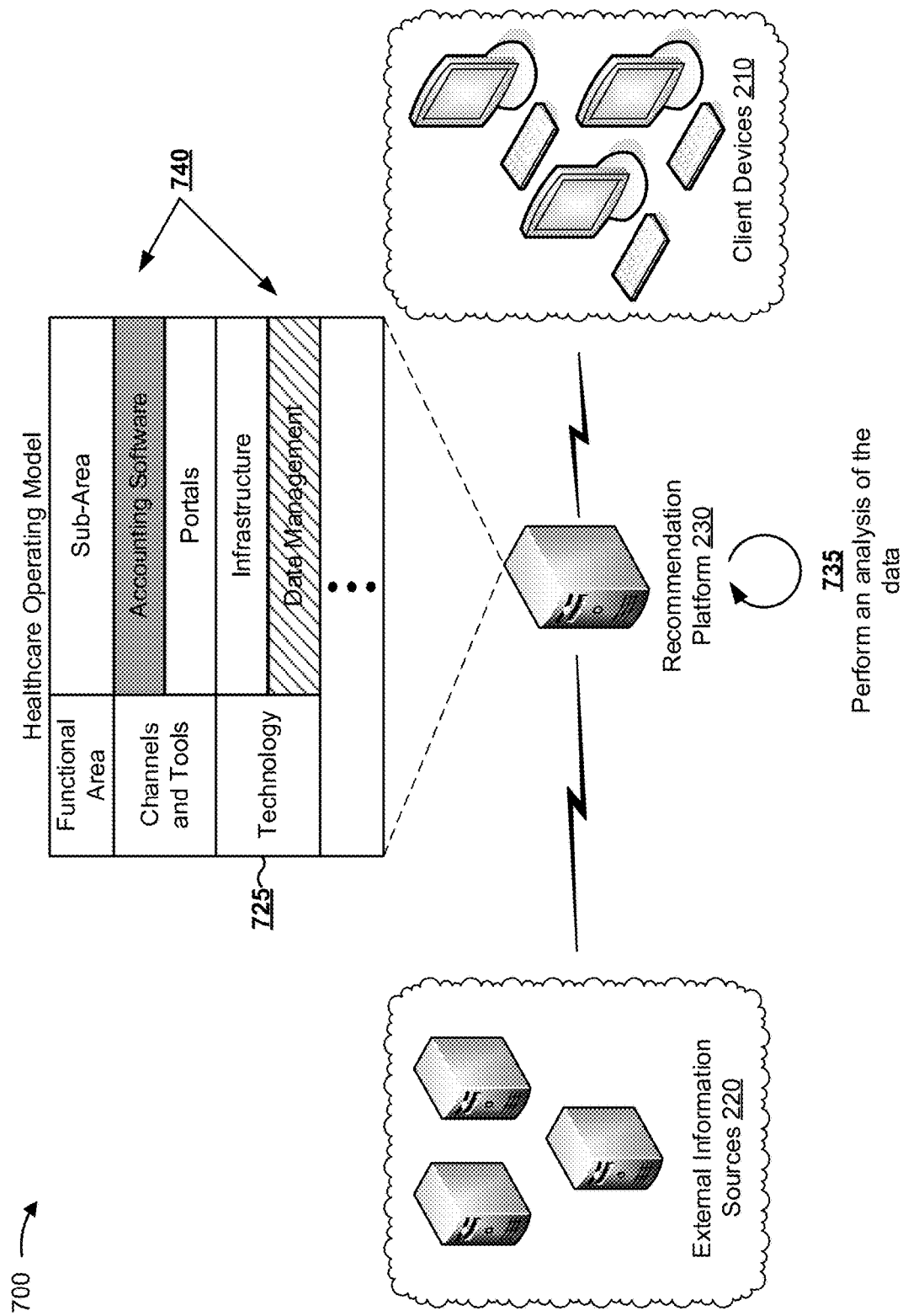

As shown in FIG. 7C, and by reference number 735, recommendation platform 230 may perform an analysis of the data. For example, recommendation platform 230 may perform an analysis to determine whether the healthcare organization is complying with reporting and/or compliance rules. Continuing with the previous example, recommendation platform 230 may identify functional areas and/or sub-areas of the organization that are satisfying reporting and/or compliance rules, do not satisfy reporting and/or compliance rules, and/or the like. In this case, as shown by reference number 740, recommendation platform 230 may identify accounting software as a sub-area for which the healthcare organization is insufficiently reporting (e.g., not meeting reporting obligations), shown as a shaded box. As further shown by reference number 740, recommendation platform 230 may identify data management as a sub-area that is sufficiently reporting (e.g., satisfying a reporting obligation), shown as a striped box.

Figure 7D:
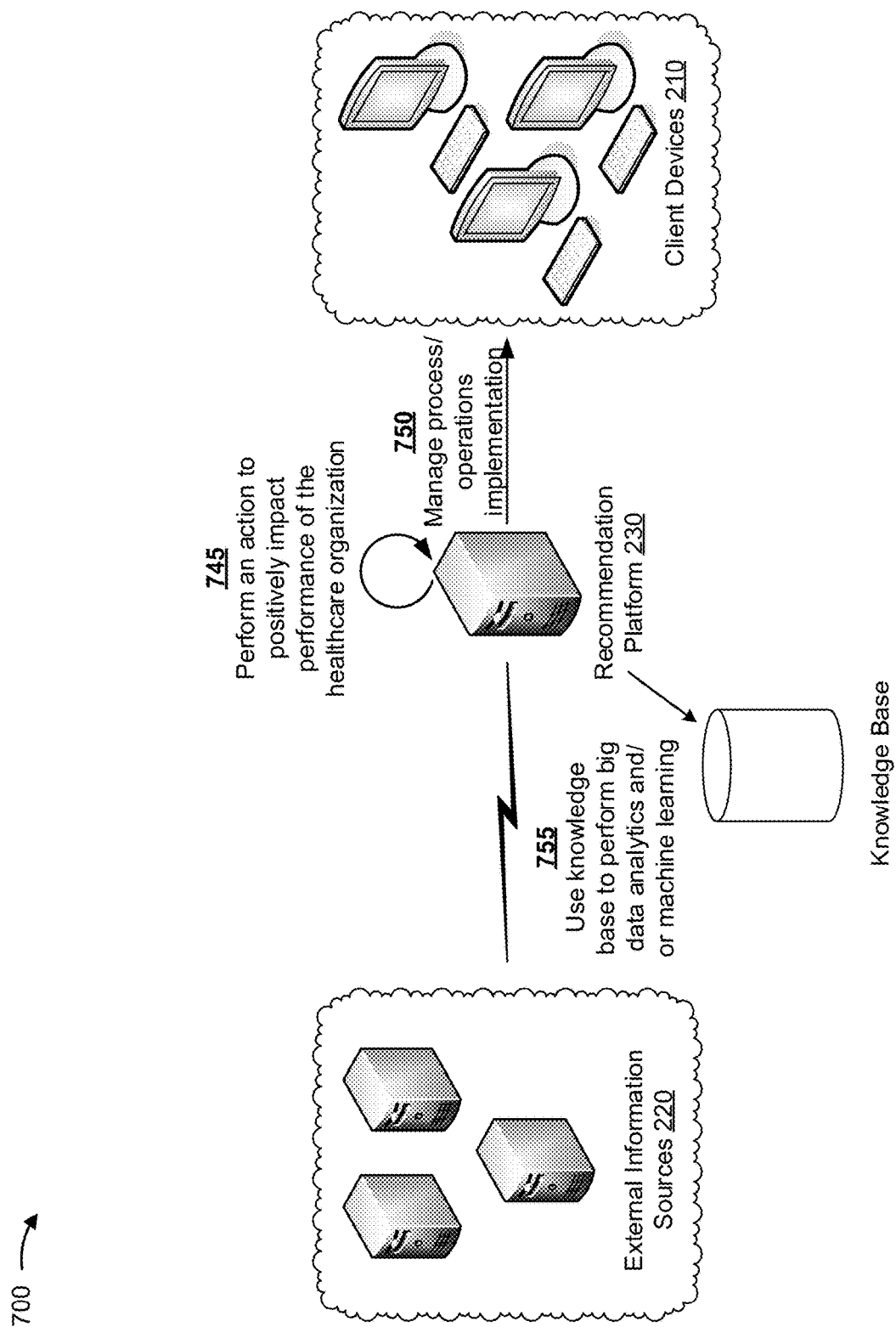

As shown in FIG. 7D, and by reference number 745, recommendation platform 230 may perform an action to positively impact performance of the healthcare organization (e.g., generate a recommendation, send a message, schedule a meeting, etc., to improve reporting and/or compliance by the healthcare organization). As shown by reference number 750, recommendation platform 230 may manage implementation of a process and/or operations of the healthcare organization (e.g., based on the analysis and/or action). As shown by reference number 755, recommendation platform 230 may use a knowledge base to perform big data analytics and/or machine learning using data from the analysis, data from managing implementation of the process and/or operations, and/or the like.

As indicated above, FIGS. 7A-7D are provided merely as an example. Other examples are possible and may differ from what was described with regard to FIGS. 7A-7D.

FIGS. 8A-8D are diagrams of an example implementation 800 relating to example process 400 shown in FIG. 4. FIGS. 8A-8D show an example of a value analysis for a healthcare organization. As shown in FIGS. 8A-8D, example implementation 800 may include client devices 210, external information sources 220, and recommendation platform 230.

Figure 8A:
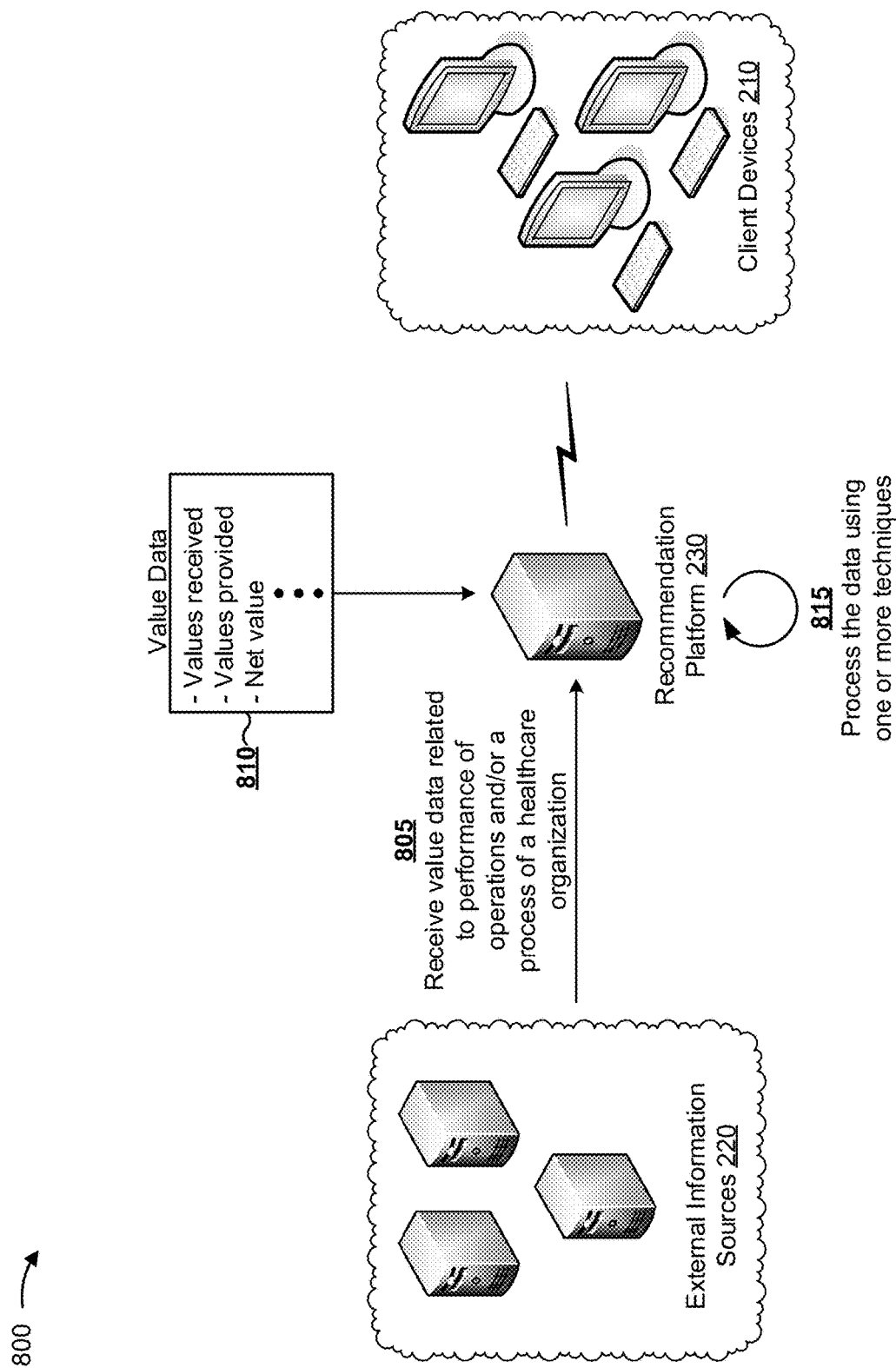
FIGS. 8A-8D are diagrams of an example implementation relating to the example process shown in FIG. 4.

As shown in FIG. 8A, and by reference number 805, recommendation platform 230 may receive value data related to performance of operations and/or a process of a healthcare organization. For example, as shown by reference number 810, the value data may identify values received by the healthcare organization, values provided by the healthcare organization, a net value, and/or the like. As shown by reference number 815, recommendation platform 230 may process the data using one or more techniques, as described elsewhere herein.

Figure 8B:
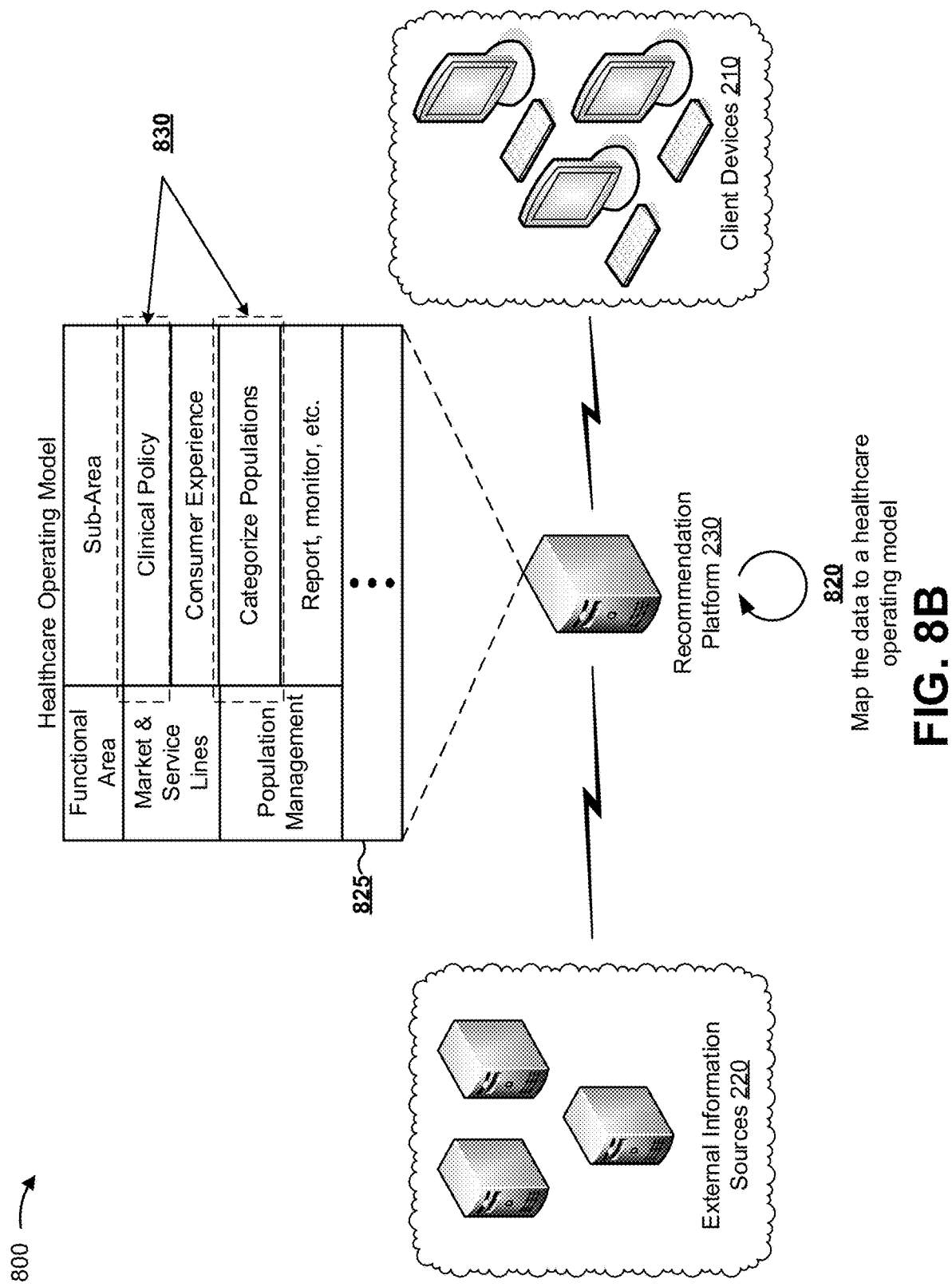

As shown in FIG. 8B, and by reference number 820, recommendation platform 230 may map the data to a healthcare operating model. For example, as shown by reference number 825, the healthcare operating model may include market and service lines as a functional area that includes clinical policy and consumer experience as sub-areas, and may include population management as a functional area that includes categorize populations and report, monitor, etc., as sub-areas. As shown by reference number 830, recommendation platform 230 may map the data to sub-areas that relate to a value analysis (e.g., clinical policy and categorize populations).

Figure 8C:
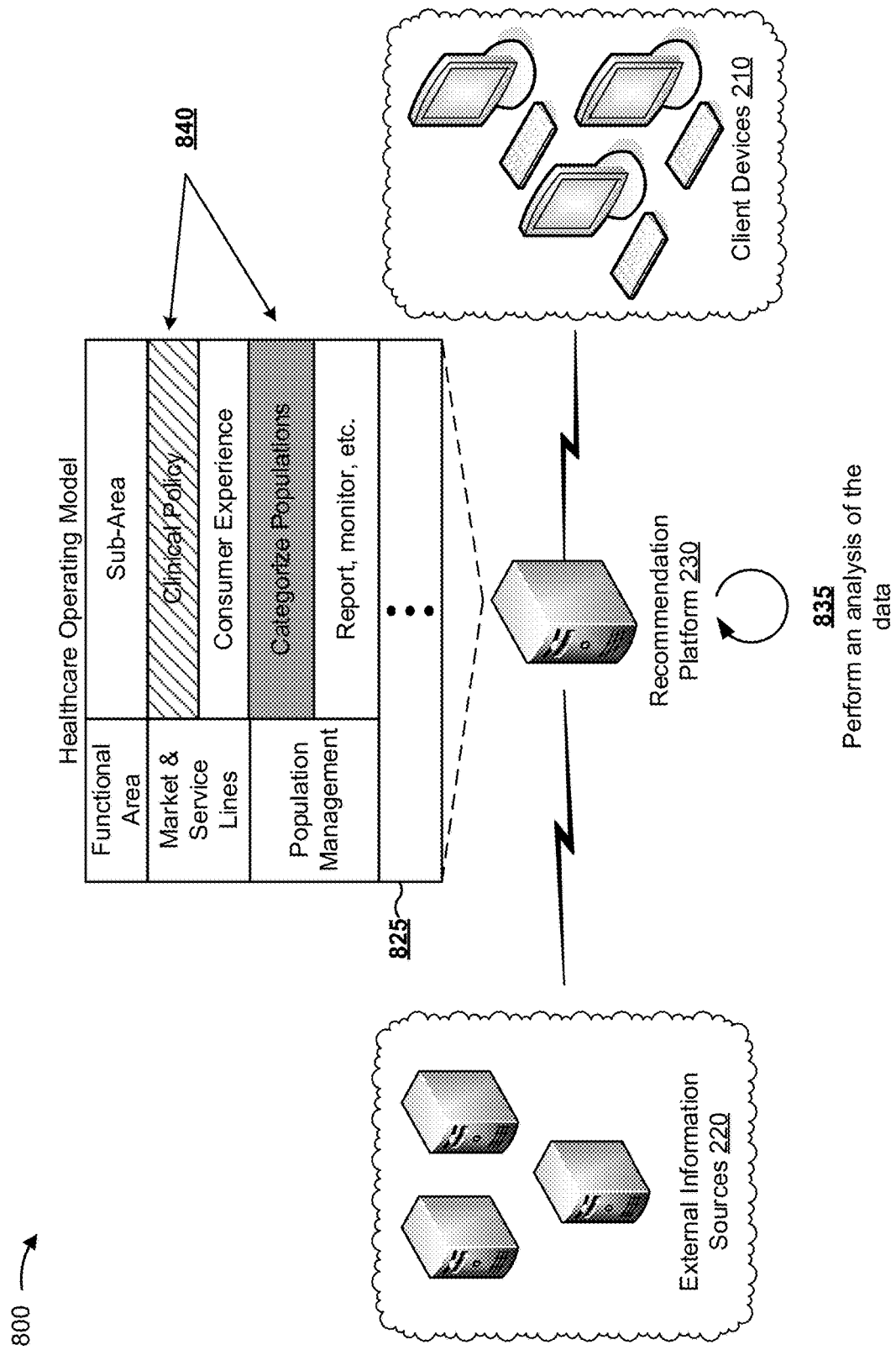

As shown in FIG. 8C, and by reference number 835, recommendation platform 230 may perform analysis of the data. For example, recommendation platform 230 may identify functional areas and/or sub-areas with a value that satisfies a threshold, a value that fails to satisfy a threshold, a value that satisfies a first threshold but not a second threshold, and/or the like. In some implementations, recommendation platform 230 may use this information to identify a processes and/or operations of the healthcare organization that are associated with a positive value or a negative value. In this case, as shown by reference number 840, recommendation platform 230 may identify categorize population as a sub-area that fails to satisfy a threshold (e.g., shown as a shaded box), and may identify clinical policy as a sub-area that satisfies a first threshold but fails to satisfy a second threshold (e.g., shown as a striped box).

Figure 8D:
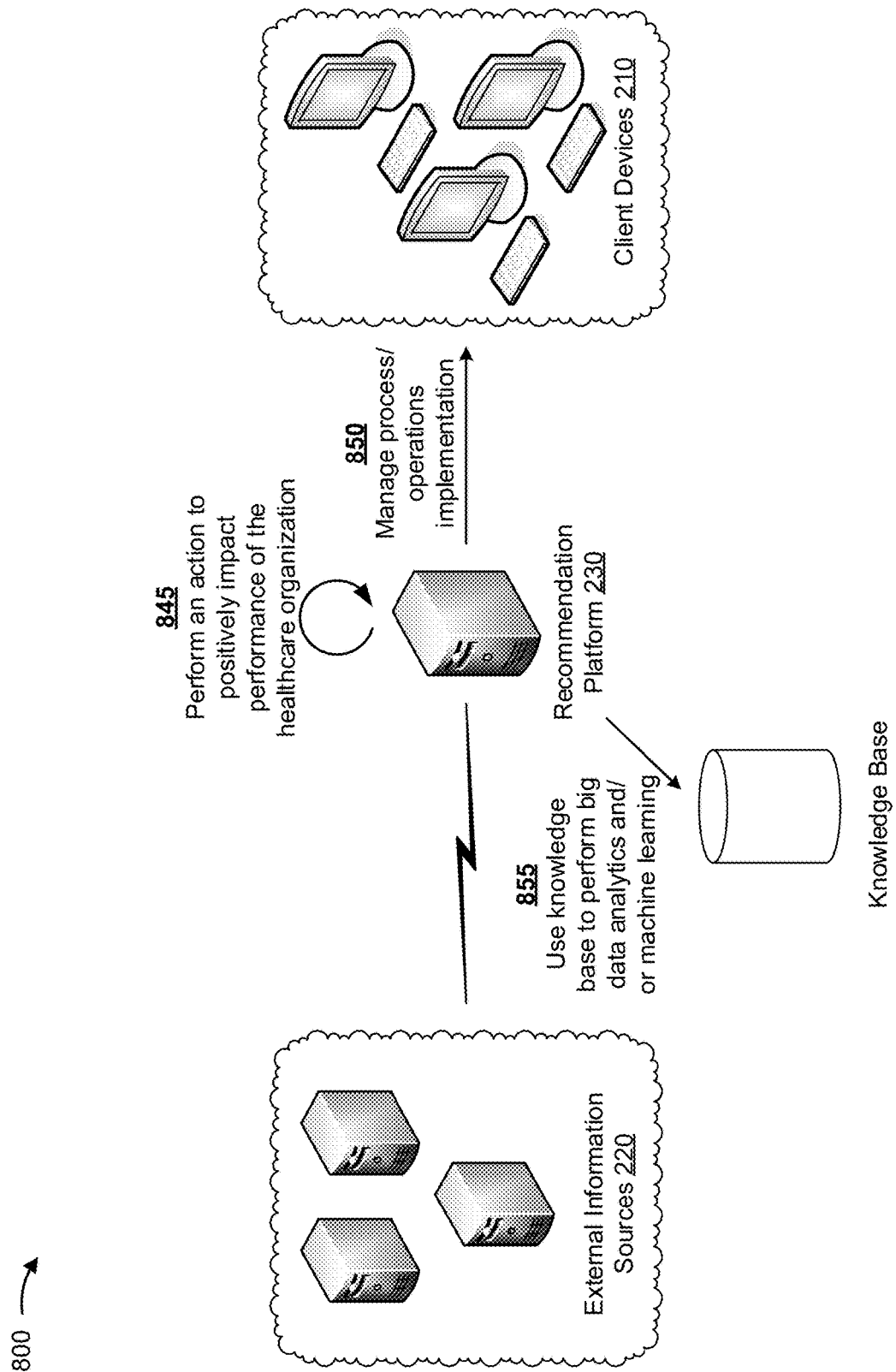

As shown in FIG. 8D, and by reference number 845, recommendation platform 230 may perform an action to positively impact performance of the healthcare organization, such as by reducing a negative value or increasing a positive value (e.g., generate a recommendation, send a message, schedule a meeting, etc., to make the processes and/or operations more profitable, be associated with a positive value, etc.). As shown by reference number 850, recommendation platform 230 may manage implementation of a process and/or operations of the healthcare organization (e.g., based on the analysis and/or action). As shown by reference number 855, recommendation platform 230 may use a knowledge base to perform big data analytics and/or machine learning using data from the analysis, data gathered when managing implementation of the process and/or operations, and/or the like.

As indicated above, FIGS. 8A-8D are provided merely as an example. Other examples are possible and may differ from what was described with regard to FIGS. 8A-8D. In addition, although example implementations 500 through 800 were described as separate examples, example implementations 500 through 800 can occur concurrently.

Implementations described herein enable a recommendation platform to receive data associated with a performance of a process of a healthcare organization and/or operations of the healthcare organization, to analyze the data to identify a deficiency related to the performance and/or a manner in which the performance can be improved, and/or to automatically perform an action to positively impact the deficiency and/or to improve the performance.

In this way, the recommendation platform increases an efficiency of analyzing a process of a healthcare organization and/or operations of the healthcare organization. In addition, this improves an accuracy of a result and/or output of a process, thereby conserving processing resources that would otherwise be consumed due to inaccurate results and/or outputs. Further, this improves performance of a process and/or operations of a healthcare organization, thereby conserving processing resources and/or computing resources of devices used to implement the process and/or the operations.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
one or more processors to:
receive data associated with an organization,
the data identifying hardware resources, of the organization, that are used to implement a process or operations of the organization;
process the data using a plurality of processing techniques,
the plurality of processing techniques comprising:
natural language processing, and
at least one of:
data reformatting, or
data normalizing, and
the plurality of processing techniques to permit mapping of the data to an operating model that represents a benchmark or industry standard relating to the process or operations of the organization;

map the data to the operating model after processing
the data,
the operating model to be used to perform an analysis of the process or the operations of the organization based on the benchmark or industry standard;
perform the analysis of the data based on mapping the data to the operating model;
identify, based on performing the analysis:
a plurality of deficiencies related to at least one of volume, storage capacity, or processing capabilities of the hardware resources, and
a corresponding manner, for each deficiency of the plurality of deficiencies, in which to modify the at least one of the volume, the storage capacity, or the processing capabilities of the hardware resources to improve a performance of the process or the operations of the organization;
generate, for each deficiency of the plurality of deficiencies, a corresponding score based on the corresponding manner;
select a particular deficiency, of the plurality of deficiencies, based on the corresponding score of each deficiency of the plurality of deficiencies; and
perform, for the particular deficiency, an action, associated with modifying the at least one of the volume, the storage capacity, or the processing capabilities of the hardware resources, to positively impact the performance of the process or the operations of the organization.

2. The device of claim 1, where the one or more processors are further to:
determine whether the organization is using a threshold amount of threshold hardware resources based on performing the analysis; and
where the one or more processors, when identifying the plurality of deficiencies, are to:
identify the plurality of deficiencies based on determining whether the organization is using the threshold amount of threshold hardware resources.

3. The device of claim 1, where the one or more processors are further to:
determine a manner in which an individual interacts with a set of systems that implement the process or operations of the organization based on mapping the data to the operating model; and
where the one or more processors, when performing the analysis of the data, are to:
perform the analysis of the data based on determining the manner in which the individual interacts with the set of systems.

4. The device of claim 1, where the one or more processors are further to:
identify a first functional area of the organization with which the data is associated based on receiving the data;
identify a second functional area of the operating model to which to map the data using machine learning or artificial intelligence, based on identifying the first functional area; and
where the one or more processors, when mapping the data to the operating model, are to:
map the data to the operating model based on identifying the second functional area.

5. The device of claim 1, where the one or more processors are further to:
store the data in a knowledge base based on performing the analysis; and
perform another analysis of another organization using the knowledge base after storing the data in the knowledge base.

6. The device of claim 1, where the one or more processors are further to:
receive other data associated with a set of other organizations prior to receiving the data;
generate the operating model based on receiving the other data; and
where the one or more processors, when receiving the data, are to:
receive the data after generating the operating model.

7. The device of claim 1, where the one or more processors are further to:
identify a type of the organization based on receiving the data,
the type including an accountable care organization or an integrated delivery organization;
select the operating model, from multiple operating models, based on identifying the type of the organization; and
where the one or more processors, when mapping the data to the operating model, are to:
map the data to the operating model based on selecting the operating model.

8. A method, comprising:
receiving, by a device, data associated with a healthcare organization,
the data identifying hardware processing resources or computing resources that are used to implement a plurality of processes or operations of the healthcare organization;
processing, by the device, the data using a plurality of processing techniques to permit mapping of the data to a healthcare operating model that represents a benchmark or industry standard relating to the process or operations of the organization,
the plurality of processing techniques including natural language processing,
the plurality of processing techniques including at least one of:
data reformatting, or
data normalizing, and
the healthcare operating model identifying a plurality of functional areas or sub-areas of a particular healthcare organization;
mapping, by the device, the data to the healthcare operating model after processing the data,
the healthcare operating model to be used to perform a plurality of analyses of the plurality of processes or operations of the healthcare organization based on the benchmark or industry standard;
performing, by the device, the plurality of analyses of the data based on mapping the data to the healthcare operating model;
identifying, by the device and based on performing the plurality of analyses:
a plurality of deficiencies related to at least one of volume, storage capacity, or processing capabilities of the hardware processing resources or the computing resources, and
a corresponding manner, for each deficiency of the plurality of deficiencies, in which to modify the at least one of the volume, the storage capacity, or the processing capabilities of the hardware processing resources or the computing resources to improve a performance of the plurality of processes or operations of the healthcare organization;

generating, by the device and for each deficiency of the plurality of deficiencies, a corresponding score based on the corresponding manner;

selecting, by the device, a particular deficiency, of the plurality of deficiencies, based on the corresponding score of each deficiency of the plurality of deficiencies; and storing, by the device, the data, or information associated with the plurality of analyses, in a knowledge base based on selecting the particular deficiency; and performing, by the device and for the particular deficiency, at least one action, associated with modifying the at least one of the volume, the storage capacity, or the processing capabilities of the hardware processing resources or the computing resources, to positively impact the performance of the plurality of processes or operations of the healthcare organization.

9. The method of claim 8, further comprising:
gathering a plurality of metrics related to the plurality of processes or operations of the healthcare organization based on performing the at least one action; and
dynamically adjusting implementation of the plurality of processes or operations of the healthcare organization based on gathering the plurality of metrics.

10. The method of claim 8, further comprising:
providing a set of instructions to a plurality of devices to modify the plurality of processes or operations of the healthcare organization based on identifying the plurality of deficiencies; and
where performing the at least one action comprises:
managing implementation of the plurality of processes or operations of the healthcare organization based on providing the set of instructions to the plurality of devices.

11. The method of claim 8, further comprising:
determining whether a first plurality of functional areas used to implement the plurality of processes or operations, matches a second plurality of functional areas used by another healthcare organization to implement a same plurality of processes or operations, based on mapping the data to the healthcare operating model; and
where identifying the plurality of deficiencies comprises:
identifying the plurality of deficiencies based on determining whether the first plurality of functional areas matches the second plurality of functional areas.

12. The method of claim 8, where the corresponding score indicates a severity for a corresponding deficiency of the plurality of deficiencies.

13. The method of claim 8, where identifying the plurality of deficiencies comprises:
identifying the plurality of deficiencies based on identifying a plurality of systems with which a plurality of individuals interact; and
where performing the at least one action comprises:
performing the at least one action to modify a manner in which the plurality of processes or operations interact with the plurality of systems.

14. The method of claim 8, further comprising:
determining whether an amount of the hardware processing resources or the computing resources satisfies a threshold; and where performing the at least one action comprises:
generating a recommendation to reduce the amount of the hardware processing resources or the computing resources based on determining whether the amount satisfies the threshold.

15. A non-transitory computer-readable medium storing instructions, the instructions comprising:
one or more instructions that, when executed by one or more processors, cause the one or more processors to:
receive data associated with one or more healthcare organizations,
the data identifying one or more hardware systems, of the one or more healthcare organizations, that are used to implement one or more processes or operations of the one or more healthcare organizations;
process the data using, a plurality of processing techniques, to permit mapping of the data to a healthcare operating model that represents a benchmark or industry standard relating to the process or operations of the organization,
the plurality of processing techniques including:
natural language processing, and
at least one of:
data reformatting, or
data normalizing;
map the data to the healthcare operating model, using one or more identifiers associated with the data after processing the data,
the healthcare operating model to be used to perform one or more analyses of the one or more processes or operations of the one or more healthcare organizations based on the benchmark or industry standard,
the one or more identifiers identifying one or more functional areas, or one or more sub-areas, of the one or more healthcare organizations with which the data is associated;
perform one or more analyses of the data to identify, based on mapping the data to the healthcare operating model:
a plurality of deficiencies related to at least one of volume, storage capacity, or processing capabilities of the one or more hardware systems, and
a corresponding manner, for each deficiency of the plurality of deficiencies, in which to modify the at least one of the volume, the storage capacity, or the processing capabilities of the one or more hardware systems to improve a performance of the one or more processes or operations;
generate, for each deficiency of the plurality of deficiencies, a corresponding score based on the corresponding manner;
select a particular deficiency, of the plurality of deficiencies, based on the corresponding score of each deficiency of the plurality of deficiencies; and
perform, for the particular deficiency, one or more actions, associated with modifying the at least one of the volume, the storage capacity, or the processing capabilities of the one or more hardware systems, to positively impact the performance of the one or more processes or operations of the one or more healthcare organizations.

16. The non-transitory computer-readable medium of claim 15, where the one or more instructions, when executed by the one or more processors, further cause the one or more processors to:

determine one or more combinations of functional areas, or sub-areas, that the one or more healthcare organizations use to implement the one or more processes or operations based on performing the one or more analyses;

determine whether the one or more combinations matches one or more other combinations identified by the healthcare operating model based on determining the one or more combinations; and where the one or more instructions, that cause the one or more processors to identify the plurality of deficiencies, cause the one or more processors to:

identify the plurality of deficiencies based on determining whether the one or more combinations matches the one or more other combinations.

17. The non-transitory computer-readable medium of claim 15, where the plurality of deficiencies relate to one or more interactions of one or more individuals with one or more call centers; and where the one or more actions are to positively impact the one or more interactions with the one or more call centers.

18. The non-transitory computer-readable medium of claim 15, where the plurality of deficiencies relate to one or more capabilities of the one or more healthcare organizations; and where the one or more actions are to positively impact the one or more capabilities of the one or more healthcare organizations.

19. The non-transitory computer-readable medium of claim 15, where the plurality of deficiencies relate to one or more reporting or compliance functions of the one or more healthcare organizations; and where the one or more actions are to positively impact the one or more reporting or compliance functions of the one or more healthcare organizations.

20. The non-transitory computer-readable medium of claim 15, where the plurality of deficiencies relate to one or more values associated with the one or more healthcare organizations; and where the one or more actions are to positively impact the one or more values associated with the one or more healthcare organizations.

\* \* \* \* \*